United States Patent
Erickson et al.

(10) Patent No.: US 7,838,283 B2
(45) Date of Patent: Nov. 23, 2010

(54) WICKING CASSETTE METHOD AND APPARATUS FOR AUTOMATED RAPID IMMUNOHISTOCHEMISTRY

(75) Inventors: Page A. Erickson, Goleta, CA (US); Michael R. Everman, Santa Barbara, CA (US); Michael S. Bell, Santa Barbara, CA (US); Kevin S. Edberg, Santa Barbara, CA (US); Matthew M. Botke, Ojai, CA (US)

(73) Assignee: Celerus Diagnostics, Inc., Goleta, CA (US)

( * ) Notice: Subject to any disclaimer, the term of this patent is extended or adjusted under 35 U.S.C. 154(b) by 311 days.

(21) Appl. No.: 11/912,095

(22) PCT Filed: Apr. 21, 2006

(86) PCT No.: PCT/US2006/015017

§ 371 (c)(1),
(2), (4) Date: Oct. 19, 2007

(87) PCT Pub. No.: WO2006/116035

PCT Pub. Date: Nov. 2, 2006

(65) Prior Publication Data

US 2008/0286753 A1    Nov. 20, 2008

Related U.S. Application Data

(60) Provisional application No. 60/673,486, filed on Apr. 21, 2005.

(51) Int. Cl.
*C12M 1/34* (2006.01)
(52) U.S. Cl. .................................................. 435/287.1
(58) Field of Classification Search ........................ None
See application file for complete search history.

(56) References Cited

U.S. PATENT DOCUMENTS

| | | |
|---|---|---|
| 2,039,219 A | 4/1936 | Hausser et al. |
| 2,741,221 A | 4/1956 | Weiskopf et al. |
| 3,192,969 A | 7/1965 | Baruch et al. |
| 3,557,077 A | 1/1971 | Brunfeldt et al. |
| 3,728,079 A | 4/1973 | Moran |
| 3,777,283 A | 12/1973 | Elkins |
| 4,034,700 A | 7/1977 | Bassett et al. |
| 4,039,775 A | 8/1977 | Andra |
| 4,043,292 A | 8/1977 | Rogers et al. |
| 4,151,809 A | 5/1979 | Johnson |
| 4,199,613 A | 4/1980 | Johnson |
| 4,200,056 A | 4/1980 | Johnson |
| 4,332,768 A | 6/1982 | Berglund |
| 4,378,333 A | 3/1983 | Laipply |
| 4,501,496 A | 2/1985 | Griffin |
| 4,505,557 A | 3/1985 | Golias |
| 4,603,114 A | 7/1986 | Hood et al. |
| 4,731,335 A | 3/1988 | Brigati |
| 4,777,020 A | 10/1988 | Brigati |
| 4,790,640 A | 12/1988 | Nason |
| 4,798,706 A | 1/1989 | Brigati |
| 4,801,431 A | 1/1989 | Cuomo et al. |
| 4,847,208 A | 7/1989 | Bogen |
| 4,985,206 A | 1/1991 | Bowman et al. |
| 5,023,187 A | 6/1991 | Koebler et al. |
| 5,068,091 A | 11/1991 | Toya |
| 5,093,557 A | 3/1992 | Lok et al. |
| 5,231,029 A | 7/1993 | Wootton et al. |
| 5,232,667 A | 8/1993 | Hieb et al. |
| 5,338,358 A | 8/1994 | Mizusawa et al. |
| 5,425,918 A | 6/1995 | Healey et al. |
| 5,436,129 A | 7/1995 | Stapleton |
| 5,482,830 A | 1/1996 | Bogart et al. |
| 5,508,200 A * | 4/1996 | Tiffany et al. .................. 436/44 |
| 5,569,607 A | 10/1996 | Simon et al. |
| 5,595,707 A | 1/1997 | Copeland et al. |

(Continued)

FOREIGN PATENT DOCUMENTS

| | | |
|---|---|---|
| EP | 0047189 B1 | 7/1985 |
| EP | 0891811 A1 | 1/1999 |
| WO | 9739328 A1 | 10/1997 |
| WO | 03/091705 A1 | 11/2003 |
| WO | 03091705 A1 | 11/2003 |
| WO | 2005/044450 A1 | 5/2005 |
| WO | 2005064309 A1 | 7/2005 |
| WO | WO 2005064309 * | 7/2005 |
| WO | 2006012498 A1 | 2/2006 |
| WO | 2006116035 A2 | 11/2006 |

(Continued)

OTHER PUBLICATIONS

European Application No. 06 750 914.1, Third Party Submission, dated Nov. 3, 2008.

(Continued)

*Primary Examiner*—Ann Y Lam
(74) *Attorney, Agent, or Firm*—Santangelo Law Offices, P.C.

(57) ABSTRACT

A sample processing system that may be configured to achieve automatic withdrawal of a substance at the end of appropriate processing sequences such as histochemical processing may involve a plurality of samples for which substances removed by moving a wicking cartridge that may have sequentially advanced absorbsant material on rolls that are advanced an appropriate amount based upon usage in sequences such as repeated elimination and reapplication of a fluidic substance perhaps through the action of capillary motion in order to refresh a microenvironment adjacent to a sample such as a biopsy or other such sample. Snap in wicking cassettes and perhaps antibody and other substances may be included to ease operator actions and to permit location specific substance applications perhaps by including single container multiple chamber multiple fluidic substance magazines, linearly disposed multiple substance source, and primary antibody cartridges.

69 Claims, 30 Drawing Sheets

U.S. PATENT DOCUMENTS

| | | | |
|---|---|---|---|
| 5,599,501 | A | 2/1997 | Carey et al. |
| 5,645,114 | A | 7/1997 | Bogen et al. |
| 5,650,327 | A | 7/1997 | Copeland et al. |
| 5,654,199 | A | 8/1997 | Copeland et al. |
| 5,654,200 | A | 8/1997 | Copeland et al. |
| 5,804,141 | A | 9/1998 | Chianese |
| 5,807,523 | A | 9/1998 | Watts et al. |
| 5,819,842 | A | 10/1998 | Potter et al. |
| 5,839,091 | A | 11/1998 | Rhett et al. |
| 5,910,288 | A | 6/1999 | Schembri |
| 5,934,885 | A | 8/1999 | Farrell et al. |
| 5,947,167 | A | 9/1999 | Bogen et al. |
| 5,948,358 | A | 9/1999 | Kalra et al. |
| 6,051,439 | A | 4/2000 | Antonenko et al. |
| 6,083,759 | A | 7/2000 | Teshima |
| 6,096,271 | A | 8/2000 | Bogen et al. |
| 6,132,685 | A | 10/2000 | Kercso et al. |
| 6,165,739 | A | 12/2000 | Clatch |
| 6,180,061 | B1 | 1/2001 | Bogen et al. |
| 6,183,693 | B1 | 2/2001 | Bogen et al. |
| 6,218,191 | B1 | 4/2001 | Palander |
| 6,296,809 | B1 | 10/2001 | Richards et al. |
| 6,349,264 | B1 | 2/2002 | Rhett et al. |
| 6,352,861 | B1 | 3/2002 | Copeland et al. |
| 6,390,292 | B2 | 5/2002 | Hawthorne |
| 6,485,917 | B1 | 6/2002 | Schermer et al. |
| 6,432,720 | B2 | 8/2002 | Chow |
| 6,451,551 | B1 | 9/2002 | Zhan et al. |
| 6,484,556 | B1 | 11/2002 | Jabobs et al. |
| 6,485,918 | B1 | 11/2002 | Schermer et al. |
| 6,495,106 | B1 | 12/2002 | Kalra et al. |
| 6,534,008 | B1 | 3/2003 | Angros |
| 6,541,261 | B1 | 4/2003 | Bogen et al. |
| 6,544,798 | B1 | 4/2003 | Christensen et al. |
| 6,582,962 | B1 | 6/2003 | Richards et al. |
| 6,594,537 | B1 | 7/2003 | Bernstein et al. |
| 6,632,598 | B1 | 10/2003 | Zhang et al. |
| 6,649,368 | B1 | 11/2003 | Aghassi |
| 6,703,247 | B1 | 3/2004 | Chu |
| 6,723,500 | B2 | 4/2004 | Yu |
| 6,735,531 | B2 | 5/2004 | Rhett et al. |
| 6,746,851 | B1 | 6/2004 | Tseung et al. |
| 6,783,733 | B2 | 8/2004 | Bogen et al. |
| 6,821,072 | B2 | 11/2004 | Thiem |
| 6,827,901 | B2 | 12/2004 | Copeland et al. |
| 6,855,292 | B2 | 2/2005 | Angros |
| 6,855,559 | B1 | 5/2005 | Christensen et al. |
| 6,905,816 | B2 | 6/2005 | Jacobs et al. |
| 6,943,029 | B2 | 9/2005 | Copeland et al. |
| 6,998,270 | B2 | 2/2006 | Tseung et al. |
| 7,067,325 | B2 | 6/2006 | Christensen et al. |
| 7,070,951 | B2 | 7/2006 | Zhang et al. |
| 7,153,474 | B2 | 12/2006 | Thiem |
| 7,250,301 | B2 | 7/2007 | Angros |
| 7,285,244 | B2 | 10/2007 | Gazeau |
| 6,833,536 | B2 | 11/2007 | Shigeura |
| 7,378,055 | B2 | 5/2008 | Lemme et al. |
| 7,396,508 | B1 | 7/2008 | Richards et al. |
| 7,410,753 | B2 | 8/2008 | Hopkins et al. |
| 7,476,543 | B2 | 1/2009 | Becker et al. |
| 7,568,514 | B2 | 8/2009 | Izvoztchikov |
| 7,635,453 | B2 | 12/2009 | Becker |
| 7,689,022 | B2 | 3/2010 | Weiner et al. |
| 2002/0142470 | A1 | 10/2002 | Clarke et al. |
| 2002/0182623 | A1 | 12/2002 | Lefevre et al. |
| 2003/0044837 | A1 | 3/2003 | Schermer et al. |
| 2003/0072682 | A1 | 4/2003 | Kikinis |
| 2003/0091477 | A1 | 5/2003 | Paul et al. |
| 2003/0124729 | A1 | 7/2003 | Christensen et al. |
| 2003/0138877 | A1 | 7/2003 | Gibbs et al. |
| 2003/0203493 | A1 | 10/2003 | Lemme et al. |
| 2004/0033163 | A1 | 2/2004 | Tseung et al. |
| 2004/0037739 | A1 | 2/2004 | McNeely et al. |
| 2004/0043495 | A1 | 3/2004 | Stokes et al. |
| 2004/0053414 | A1 | 3/2004 | Devlin, Sr. |
| 2004/0191128 | A1 | 9/2004 | Bogen et al. |
| 2004/0241050 | A1 | 12/2004 | Bogen et al. |
| 2005/0281711 | A1 | 12/2005 | Testa et al. |
| 2006/0019302 | A1 | 1/2006 | Lemme et al. |
| 2006/0029519 | A1 | 2/2006 | Nakaya |
| 2006/0134793 | A1 | 2/2006 | Key et al. |
| 2006/0001930 | A1 | 5/2006 | Yeh et al. |
| 2006/0239858 | A1 | 10/2006 | Becker |
| 2006/0239868 | A1 | 10/2006 | Sage et al. |
| 2006/0252025 | A1 | 11/2006 | Nitta et al. |
| 2007/0243603 | A1 | 10/2007 | Einsle et al. |
| 2007/0272710 | A1 | 11/2007 | Bui et al. |
| 2008/0261266 | A1 | 10/2008 | Kram et al. |
| 2009/0004691 | A1* | 1/2009 | Erickson et al. ............ 435/40.5 |
| 2009/0117611 | A1 | 5/2009 | Becker et al. |
| 2009/0170152 | A1 | 7/2009 | Reeser et al. |

FOREIGN PATENT DOCUMENTS

| | | |
|---|---|---|
| WO | 2006116035 A3 | 11/2006 |
| WO | 2006116037 A2 | 11/2006 |
| WO | 2006116037 A3 | 11/2006 |
| WO | 2006116039 A2 | 11/2006 |
| WO | 2006116039 A3 | 11/2006 |
| WO | 2006116199 A2 | 11/2006 |
| WO | 2006116199 A3 | 11/2006 |
| WO | 2008055096 A3 | 5/2008 |
| WO | 2006007841 | 1/2009 |
| WO | 2009085842 A1 | 7/2009 |
| WO | 2009086048 A1 | 7/2009 |

OTHER PUBLICATIONS

Office Action for U.S. Appl. No. 11/912,273, filed May 4, 2010.
Written Opinion for International Application No. PCT2006/015023 dated Oct. 31, 2006.
Written Opinion for International Application No. PCT2006/015017 dated Sep. 20, 2007.
U.S. Appl. No. 60/673,468, filed Apr. 21, 2005.
International Application No. PCT/EP03/04192, Search Report dated Feb. 21, 2003, filed here as part of the International Publication No. WO 03/091705 A1: publication date Nov. 6, 2003.
International Application No. PCT/EP03/04192, International Preliminary Examination Report dated Jun. 24, 2004, Translated to English.
International Application No. PCT/EP2004/012455, Search Report dated Jan. 28, 2005, filed here as part of the International Publication No. WO 2005/044450 A1, publication date May 9, 2005.
International Application No. PCT/EP2004/012455, International Preliminary Report on Patentability Translated to English dated Mar. 6, 2006.
International Application No. PCT/US2006/015017, International Preliminary Report on Patentability dated Nov. 6, 2007.
U.S. Appl. No. 11/911,946, Non-final Office Action dated Jun. 17, 2010.
U.S. Appl. No. 11/911,946, Interview Summary dated Jul. 1, 2010.
U.S. Appl. No. 11/912,273 Non-final Office Action dated Jun. 25, 2010.
U.S. Appl. No. 11/912,273, Interview Summary dated Jun. 3, 2010.
International Patent Application No. PCT/US2010/035159; International Search Report dated Jul. 14, 2010.
International Patent Application No. PCT/US2010/035159; Written Opinion of the International Searching Authority dated Jul. 14, 2010.
U.S. Appl. No. 11/912,273, Interview Summary dated Jul. 1, 2010.
Parallel China Patent Application No. 200680022409.7; office action dated Aug. 9, 2010.

* cited by examiner

| Step | Step Name | Move Time (Open, ms) | Dwell Time (ms) | Move Time (Close, ms) | Dwell Time (ms) | Repeats | Total Time in Step (ms) | Comments |
|---|---|---|---|---|---|---|---|---|
| 1 | Wick | 500 | 4,000 | 500 | 0 | 1 | 5,000 | |
| 2 | Dispense Ab1 | 1,000 | 8,000 | 1,000 | 0 | 1 | 10,000 | |
| 3 | Waves, Set 1 | 400 | 1,500 | 400 | 2,000 | 3 | 12900 | |
| 4 | Waves, Set 2 | 400 | 1,500 | 400 | 22,000 | 6 | 145800 | |
| 5 | Wick | 500 | 4,000 | 500 | 0 | 1 | 5,000 | |
| 6 | Dispense Buffer | 1,000 | 8,000 | 1,000 | 0 | 1 | 10,000 | |
| 7 | Waves, Set 1 | 400 | 1,500 | 400 | 4,000 | 3 | 18900 | |
| 8 | Wick | 500 | 4,000 | 500 | 0 | 1 | 5,000 | |
| 9 | Dispense Buffer | 1,000 | 8,000 | 1,000 | 0 | 1 | 10,000 | |
| 10 | Waves, Set 1 | 400 | 1,500 | 400 | 4,000 | 3 | 18900 | |
| 11 | Wick | 500 | 4,000 | 500 | 0 | 1 | 5,000 | |
| 12 | Dispense Ab2-Enz | 1,000 | 8,000 | 1,000 | 0 | 1 | 10,000 | |
| 13 | Waves, Set 1 | 400 | 1,500 | 400 | 2,000 | 3 | 12900 | |
| 14 | Waves, Set 2 | 400 | 1,500 | 400 | 22,000 | 6 | 145800 | |
| 15 | Wick | 500 | 4,000 | 500 | 0 | 1 | 5,000 | |
| 16 | Dispense Buffer | 1,000 | 8,000 | 1,000 | 0 | 1 | 10,000 | |
| 17 | Waves, Set 1 | 400 | 1,500 | 400 | 4,000 | 3 | 18900 | |
| 18 | Wick | 500 | 4,000 | 500 | 0 | 1 | 5,000 | |
| 19 | Dispense Buffer | 1,000 | 8,000 | 1,000 | 0 | 1 | 10,000 | |
| 20 | Waves, Set 1 | 400 | 1,500 | 400 | 4,000 | 3 | 18900 | |
| 21 | Wick | 500 | 4,000 | 500 | 0 | 1 | 5,000 | |
| 22 | Dispense Chromogen | 1,000 | 8,000 | 1,000 | 0 | 1 | 10,000 | |
| 23 | Waves, Set 1 | 400 | 1,500 | 400 | 2,000 | 4 | 17200 | |
| 24 | Waves, Set 2 | 400 | 1,500 | 400 | 22,000 | 6 | 145800 | |
| 25 | Wick | 500 | 4,000 | 500 | 0 | 1 | 5,000 | |
| 26 | Dispense Buffer | 1,000 | 8,000 | 1,000 | 0 | 1 | 10,000 | |
| 27 | Waves, Set 1 | 400 | 1,500 | 400 | 4,000 | 3 | 18900 | |
| 28 | Wick | 500 | 4,000 | 500 | 0 | 1 | 5,000 | |
| 29 | Dispense Buffer | 1,000 | 8,000 | 1,000 | 0 | 1 | 10,000 | |
| 30 | Waves, Set 1 | 400 | 1,500 | 400 | 4,000 | 3 | 18900 | |
| 31 | Wick | 500 | 4,000 | 500 | 0 | 1 | 5,000 | |
| 32 | Dispense Counterstain | 1,000 | 8,000 | 1,000 | 0 | 1 | 10,000 | |
| 33 | Waves, Set 1 | 400 | 1,500 | 400 | 4,000 | 4 | 25200 | |
| 34 | Wick | 500 | 4,000 | 500 | 0 | 1 | 5,000 | |
| 35 | Dispense Buffer | 1,000 | 8,000 | 1,000 | 0 | 1 | 10,000 | |
| 36 | Waves, Set 1 | 400 | 1,500 | 400 | 4,000 | 3 | 18900 | |
| 37 | Wick | 500 | 4,000 | 500 | 0 | 1 | 5,000 | |
| 38 | Dispense Buffer | 1,000 | 8,000 | 1,000 | 0 | 1 | 10,000 | |
| 39 | Waves, Set 1 | 400 | 1,500 | 400 | 4,000 | 3 | 18900 | |
| 40 | Wick | 500 | 4,000 | 500 | 0 | 1 | 5,000 | |
| 41 | Dispense Buffer | 1,000 | 8,000 | 1,000 | 4,000 | 1 | 10,000 | |
| 42 | Home | 0 | 0 | 0 | 0 | 1 | 4400 | |
| 44 | Total Time in Protocol | | | | | | 856,200 | (=Total Time in Protocol in ms: 14.27min) |

Fig. 6

WICKING CASSETTE METHOD AND APPARATUS FOR AUTOMATED RAPID IMMUNOHISTOCHEMISTRY

This application is the United States National Stage of International Application No. PCT/US2006/015017, filed Apr. 21, 2006, which claims the benefit of U.S. Provisional Patent Application No. 60/673,486, filed Apr. 21, 2005, each hereby incorporated by reference herein.

1. TECHNICAL FIELD

This invention relates to the field of automated sample testing such as may be used in biochemistry, perhaps including cytochemistry, histochemistry, and the like. Specifically, it relates to systems and devices that may be used to achieve results in a more rapid fashion, and are easier to use. Such systems and devices may be particularly appropriate for use in a surgical or operative environment, where rapids results may be necessary. Furthermore, this application addresses only certain aspects of the technology disclosed. Other aspects are addressed in the concurrently filed applications entitled: "Enhanced Fluidic Method and Apparatus for Automated Rapid Immunohistochemistry" serial number PCT/US2006/015020, "Parallel Processing Fluidic Method and Apparatus for Automated Rapid Immunohistochemistry" serial number PCT/US2006/015269, and "Method and Apparatus for Automated Rapid Immunohistochemistry" serial number PCT/US2006/015023 Each of these are hereby incorporated by reference as well as the priority filing (which this filing claims the benefit of), U.S. Provisional Application No. 60/673,468 entitled "Method and Apparatus for Automated Rapid Immunohistoc

2. BACKGROUND

Frequently during surgery, tissue biopsy samples may be removed from a patient and sent from the operating room to a pathology laboratory for analysis, for example by frozen tissue section diagnosis. In addition, methodology for frozen tissue section diagnosis may consist of freezing tissue in a pathology lab, sectioning the frozen tissue, and performing standard Hematoxylin and Eosin (H&E) staining. H&E may be a general-purpose stain for helping a medical pathologist diagnose tissue pathologies. However, H&E staining may have a number of limitations, for example that it may be a non-specific tissue stain, and may not identify specific proteins in tissue. Such identification of specific proteins in tissue, for example by using a procedure sometimes referred to as immunohistochemistry (IHC), may help a pathologist diagnose numerous intraoperative tissue pathologies. Examples may include sentinel lymph node biopsies (for potential metastatic carcinomas and melanomas), undifferentiated tumors (potential carcinomas, lymphomas, and melanomas), and biopsies of margins (looking at the edges of excised tissue to see if the entire tumor has been removed).

A problem may be that current automated IHC may require 60 to 120 minutes, which may be too long to be useful during intraoperative procedures. Intraoperative guidelines, such as those provided by the College of American Pathologists, may typically recommend reporting pathology data to the surgeon within approximately 20 minutes. Another problem is that different reagents need to be used with different tests. Operators can sometimes make mistakes and so a simplified manner of operation is desired.

It often may be difficult to examine unstained cell and tissue preparations with a microscope, for example perhaps due to a lack of contrast between individual cells and the background matrix, or perhaps between individual parts of cells. To improve such contrast, researchers may apply stains to cell and tissue specimens to be examined. Such stains may be adsorbed differently by various structures in cells, perhaps such that the contrast between the different cell structures may be improved.

Staining tissue specimens may be a nontrivial, time-consuming process. Often, a number of different staining and rinsing stages may be required. Each stage may require a specific amount and perhaps different types of reagent or buffer and may take a specific amount of time. Furthermore, at the completion of a test sequence removed material can be a hazardous material that requires specific handling and disposal. Thus, trained technicians often may be employed to perform such operations. Furthermore, hospitals and laboratories may be required to stain large numbers of tissue specimens with different reagents or substances. Thus, it may be desirable to automate the tissue specimen staining process and to make insertion of desired substances easier and more foolproof. By automating the process, expensive human labor may be eliminated and the probability of an error occurring during the staining process may be reduced. Accordingly, some manufacturers have introduced equipment for the automated staining of tissue specimens on microscope slides.

However, existing automatic staining devices may not be simple to use. Such existing automatic staining devices may required arcane programming commands and complicated procedures, which may require extensive user training before such devices can be operated effectively. Waste material can also require special handling. It therefore may be desirable to simplify the operation of an automatic staining device as well as its set up and clean up.

As mentioned earlier, though, existing automatic staining devices can take a significant amount of time to achieve a desired result. When using interacting or perhaps binding substances, such as antibodies, or more generally reagents, the substance used that may take a significant period of time to achieve its chemical result relative to an intraoperative procedure. For example, a typical reagent binding profile using an accelerated incubation period can take in excess of 60 minutes or the like. This is usually too long to leave a patient exposed and so it is not uncommon for the patient to be sewn back up and asked to return once results are available. Furthermore it may not be practical to run a bulk processing system for only one or two samples. While this testing time period may be necessary in order to achieve an amount of binding or other interaction desired with most substances, such a period of time is not typically acceptable from the perspective of performing an intraoperative procedure on a patient. Beyond merely the chemical interaction time period, the entire process can take even significantly longer. Thus it is not uncommon for many staining or other biochemical procedures to require at least one hour in order to yield the desired results.

Furthermore, the entire process may be fairly involved. For example, a biochemical process can sometimes involve steps including: subjecting a sample to a first antibody substance, perhaps driving the antibody substance around with an air knife to blow air across the surface of the sample, withdrawing the antibody substance, rinsing the sample with a buffer, subjecting the sample to a second antibody substance, perhaps again driving the antibody substance around with an air knife, withdrawing the second antibody substance, again rinsing the sample with a buffer, subjecting the sample to a chromogen substance, withdrawing the chromogen substance, again rinsing the sample with a buffer, subjecting the sample to a counterstain, withdrawing the counterstain, and then perhaps again rinsing the sample with a buffer. Each of these steps may take a significant amount of time in and of themselves, and may result in the sum of the entire procedure taking an inordinate amount of time. In fact, it may not be uncommon for such involved procedures to take 90 minutes or more. Although there may have been efforts to shorten this time period, the simple fact of the chemistry involved may have focused these efforts to some degree on speeding up the mechanical processes involved.

One process which may be known to speed up the chemical process, however, is to heat a sample and the substance applied. In this type of a system, a reagent may be heated and this may reduce the reagent-tissue interaction period. Disadvantages to heating may include the fact that many reagents and some samples may not react well to heating.

While the use of an air knife to blow air across the surface of a reagent and to drive the reagent or other substance around on the surface of the sample may have accomplished some shortening of the overall process, it remains a fact that even when this function is employed, the procedures still require long time periods on the order to 60 to 120 minutes. Thus, one of the challenges and one of the limitations of many of the automated histochemical and other such systems previously in use is the fact that they simply do not yield their results in a short enough time period in order to provide systems that can be used effectively in an intraoperative environment. Prior to the present invention, it may have even been perceived as a necessary incident to the basic chemistry that such tests required this long a time frame. In view of the foregoing, there is a need for the availability of an automated rapid IHC or other such system that would allow IHC or the like to be performed within 20 minutes or less. Automated rapid IHC or other such biochemical tests are, of course, also desired by research laboratories for frozen tissues and the like.

3. SUMMARY DISCLOSURE OF THE INVENTION

In embodiments, the present invention involves a self contained rapid sample processing system such as shown in FIG. 1. This system can be used to perform rapid IHC and may be easily used within an operator environment. Embodiments can overcome problems that have seemed insurmountable perhaps by approaching the problem from a very different perspective. The present invention presents systems in a variety of embodiments through which sample processing can be accomplished in a variety of biochemical contexts and in a dramatically shorter time period and in a manner that is easier for the operator. In fact, the present invention shortens tests that have previously taken 60 or 90 or even 120 minutes to an intraoperative time frame such as 20 minutes or the like. Embodiments of the invention overcome what may have been previously considered a physical requirement, namely, that many particular biochemistries involved simply required a long time. Embodiments of the invention also permit coincidental processing of all samples at once. Furthermore, by creating particular conditions within the system, the desired amount of chemical interactions can be accomplished in a far shortened timeframe. In embodiments, the invention acts to replenish a microenvironment on an exterior sample area of a sample so that binding or more generally, other interaction, can occur more rapidly. Embodiments of the present invention overcome the longer binding times previously perhaps taken as a physical constant. Embodiments realize that by acting in a manner to replenish a microenvironment, not just move fluid on a sample, can significantly shorten the time needed for a particular amount of interaction. Rather than using a completely new application of reagents or the like, the present invention acts in a manner where the microenvironment is replenished and a shortened interaction is achieved. Some embodiments of the invention achieve this by removing, perhaps mixing, and reapplying the same fluid so that the fluid and the substance in the microenvironment immediately adjacent the sample is not depleted. Embodiments provide snap in reagents and snap in wicking elements to facilitate operator use of the system.

4. BRIEF DESCRIPTION OF THE DRAWINGS

FIGS. 4 a-d show a depiction of surface movement sequences such as in one embodiment that act to eliminate and replenish a fluidic substance.

Figure 5:
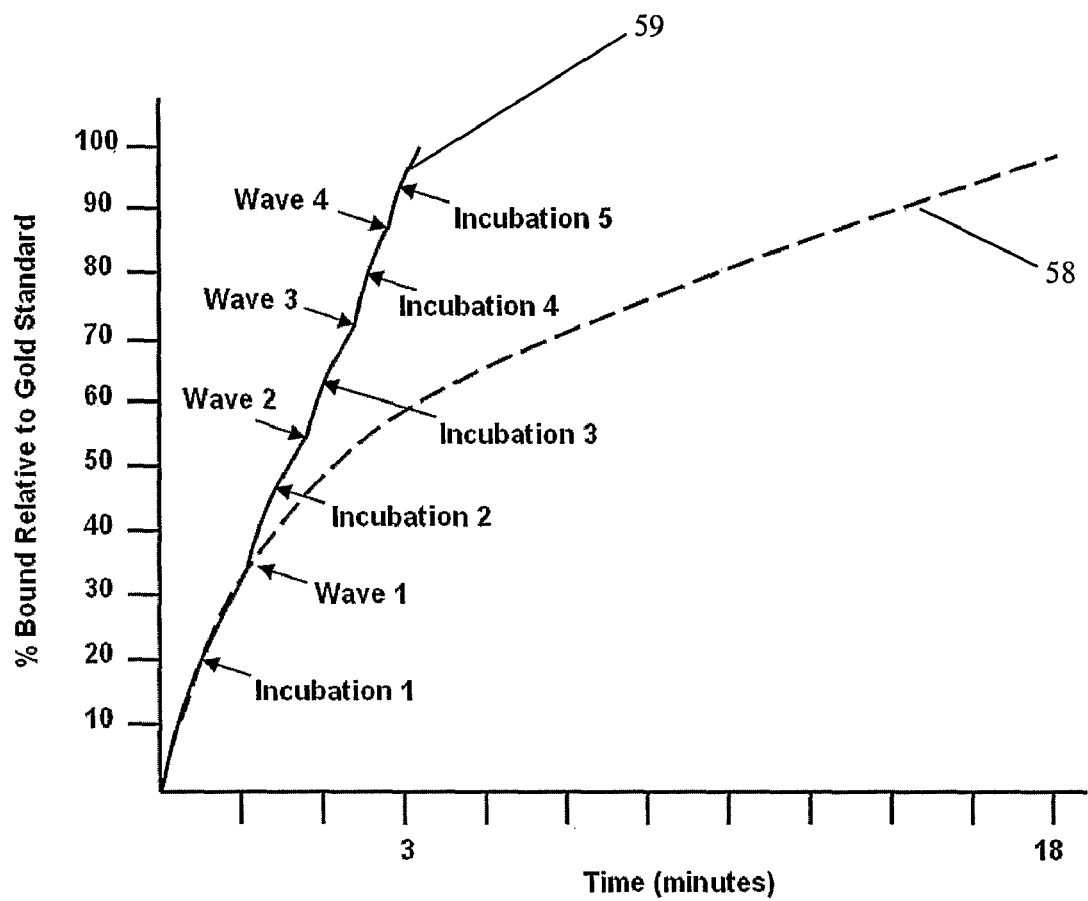

FIG. 5 is a diagram of some representative antibody binding profiles.

FIG. 6 is a depiction of some rapid sample processing protocol steps and timings.

Figure 7:
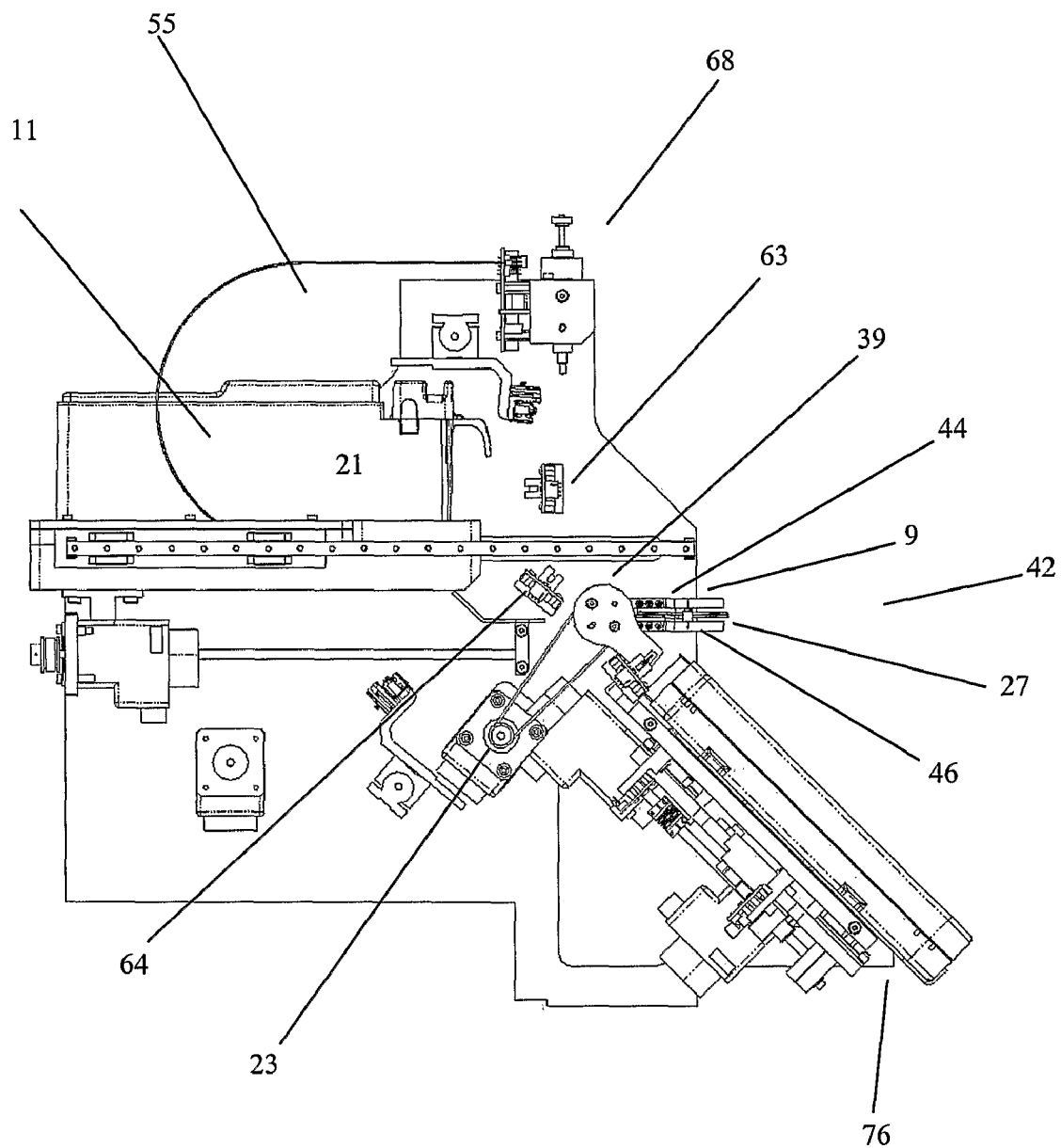

FIG. 7 is a cut away depiction of one embodiment of a rapid sample processing system.

Figure 8:
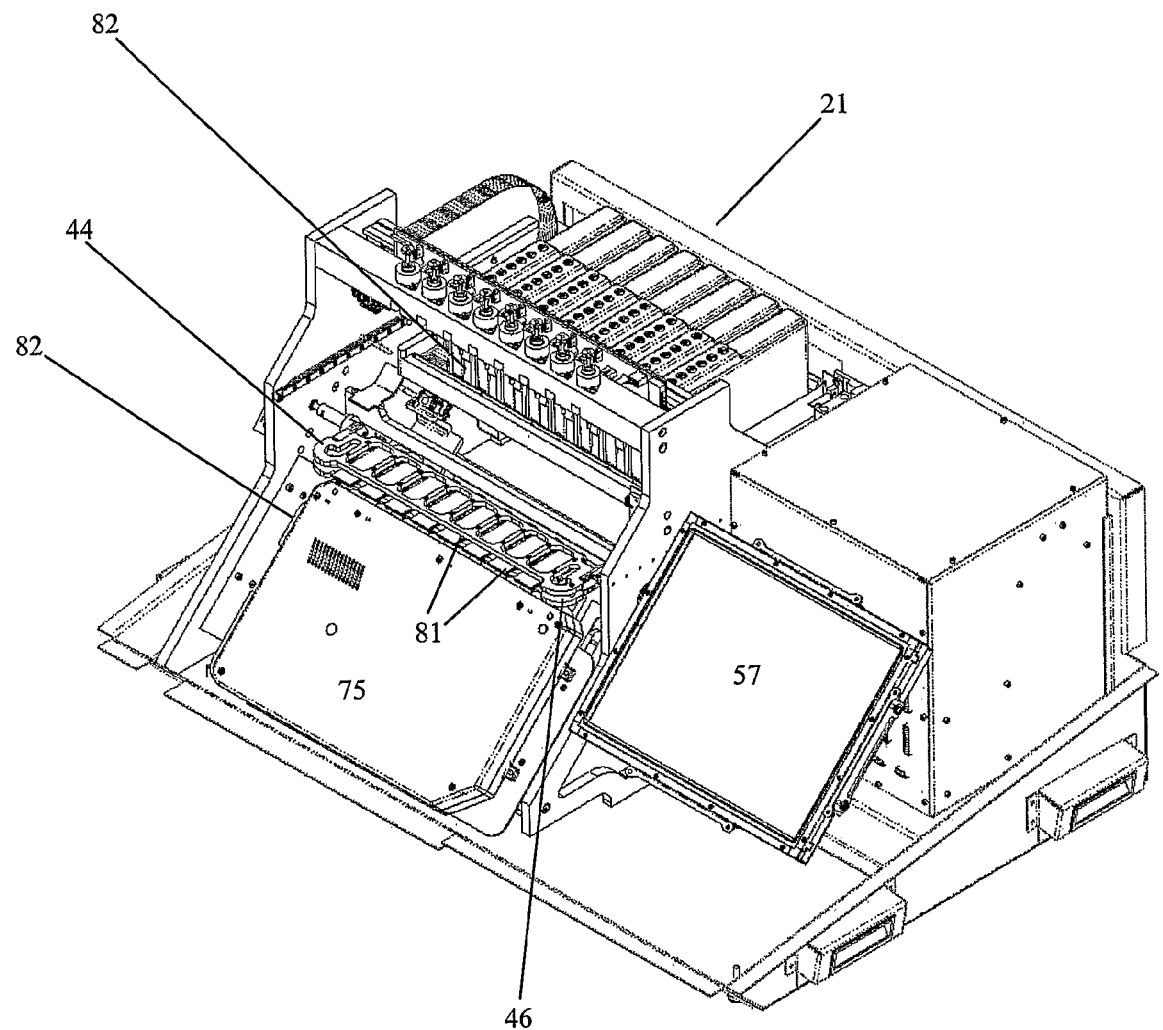

FIG. 8 is an exploded view of the embodiment of the rapid sample processing system in FIG. 7.

Figure 9:
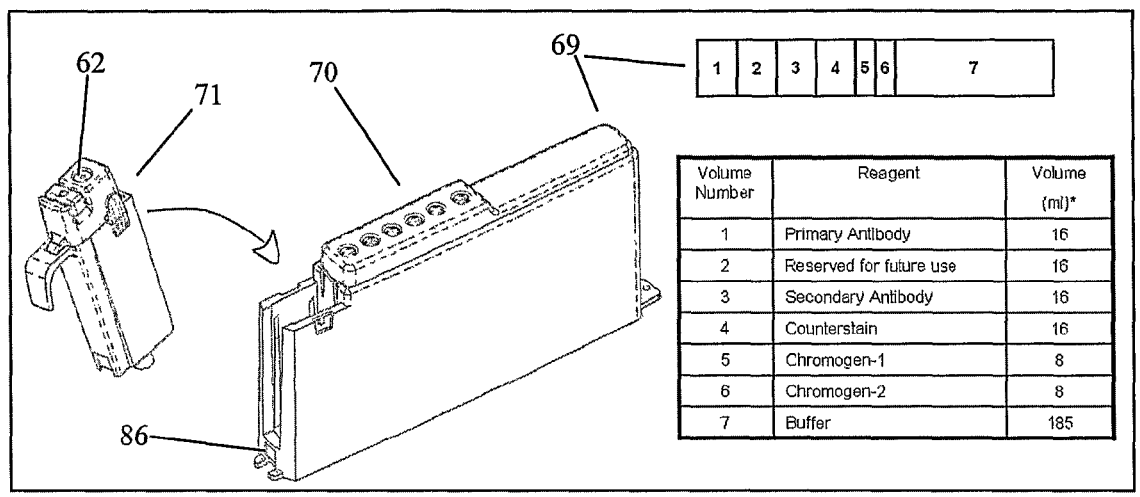

FIG. 9 is a depiction of a reagent magazine and cartridge showing use with various substances.

Figure 10:
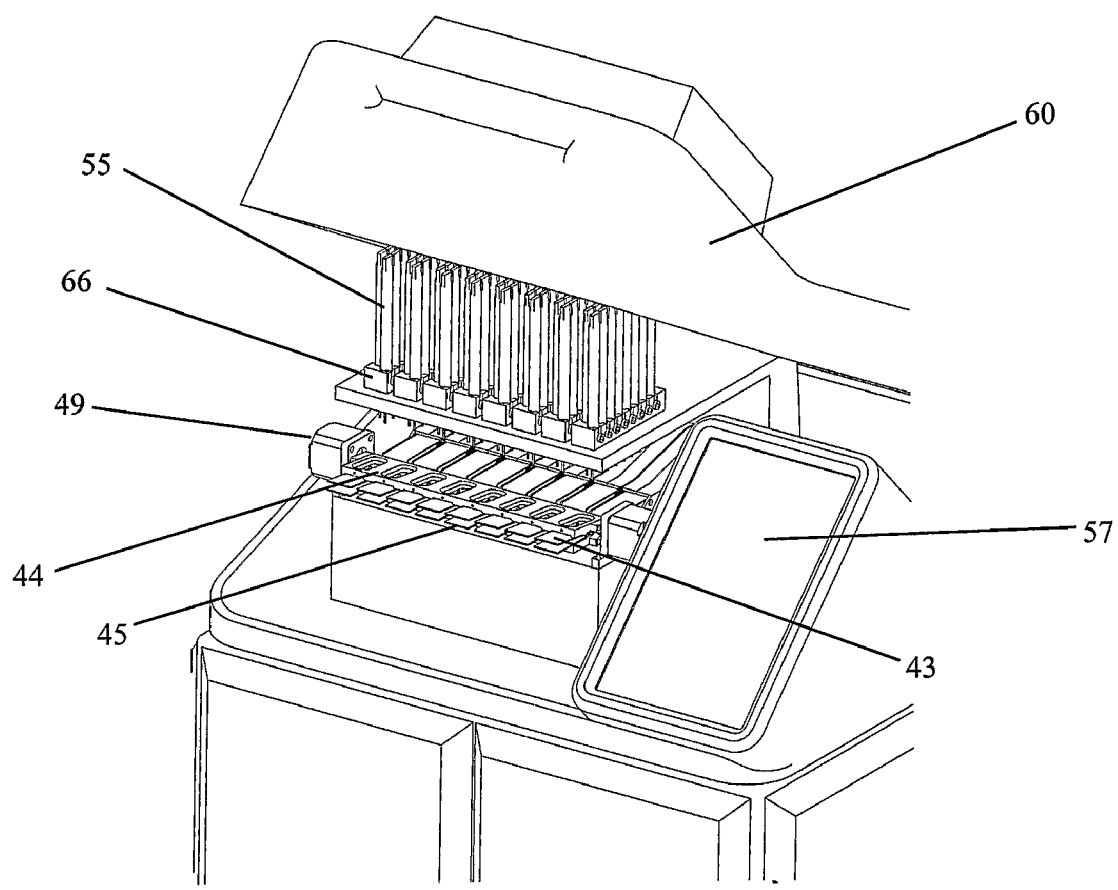

FIG. 10 shows a depiction of an instrument view of a rapid sample processing system showing certain structural elements in another embodiment.

Figure 11:
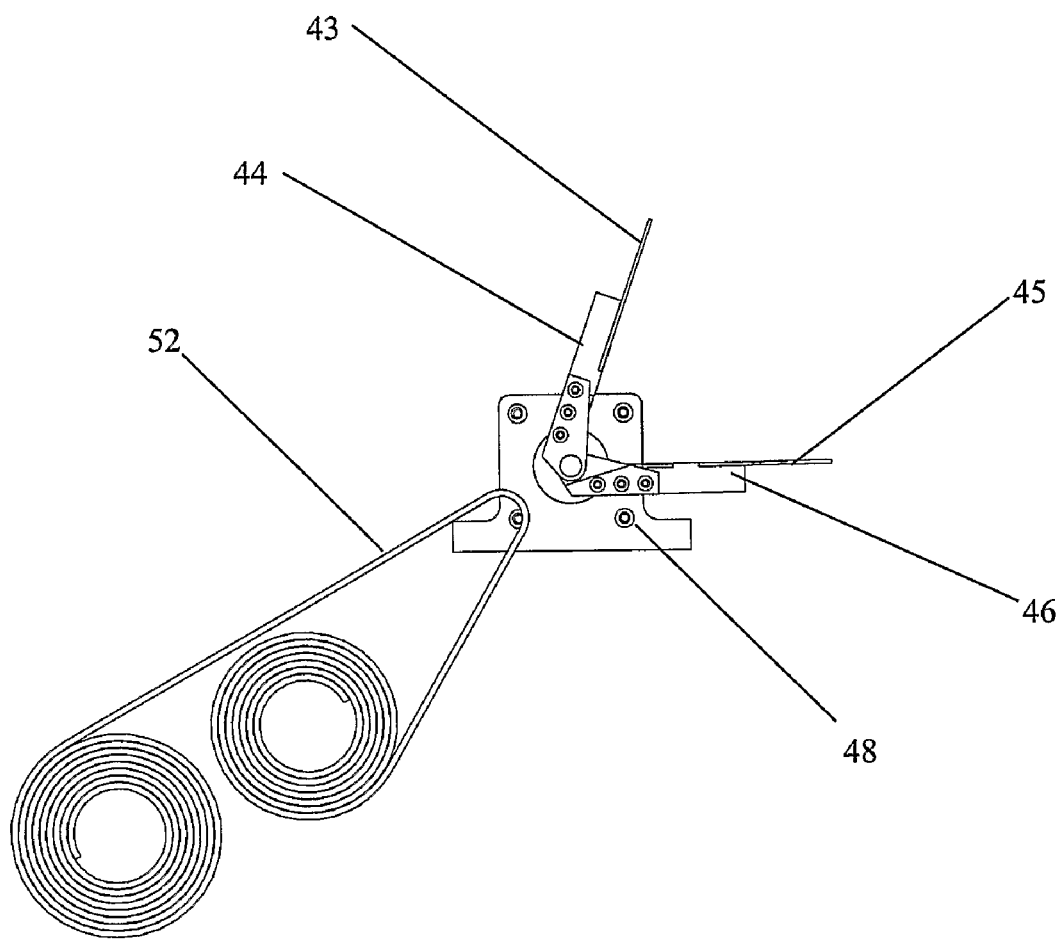

FIG. 11 shows a depiction of a side view of a slide movement system in an open position for the embodiment in FIG. 10.

Figure 12:
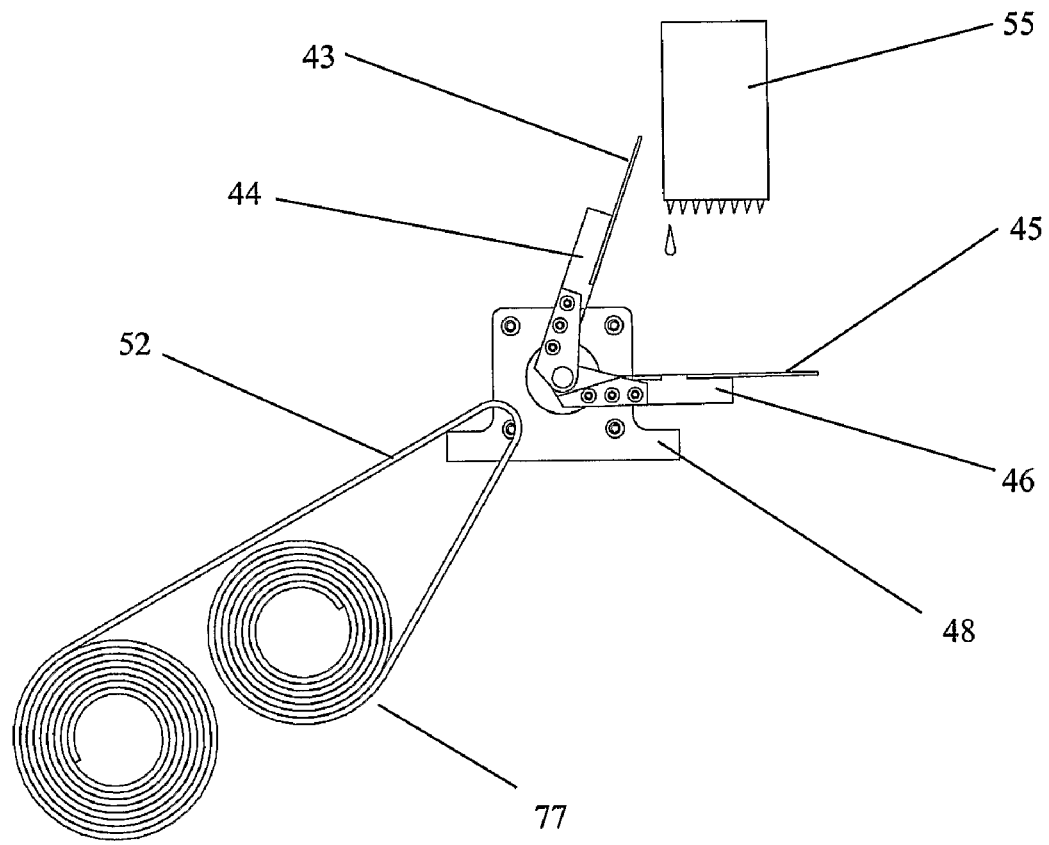

FIG. 12 shows a depiction of a side view of a slide movement system in a dispensing position for the embodiment in FIG. 10.

Figure 13:
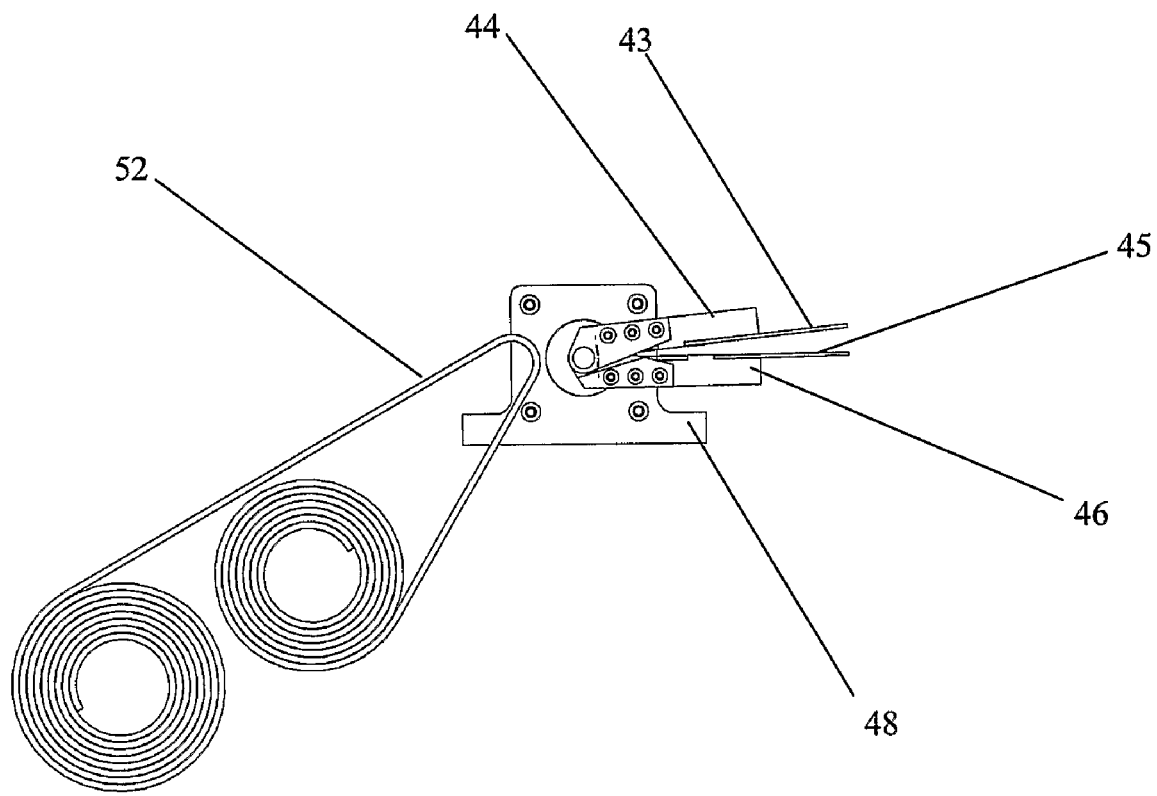

FIG. 13 is a depiction of a side view of a slide movement system in a partially closed or partially open position for the embodiment in FIG. 10.

Figure 14:
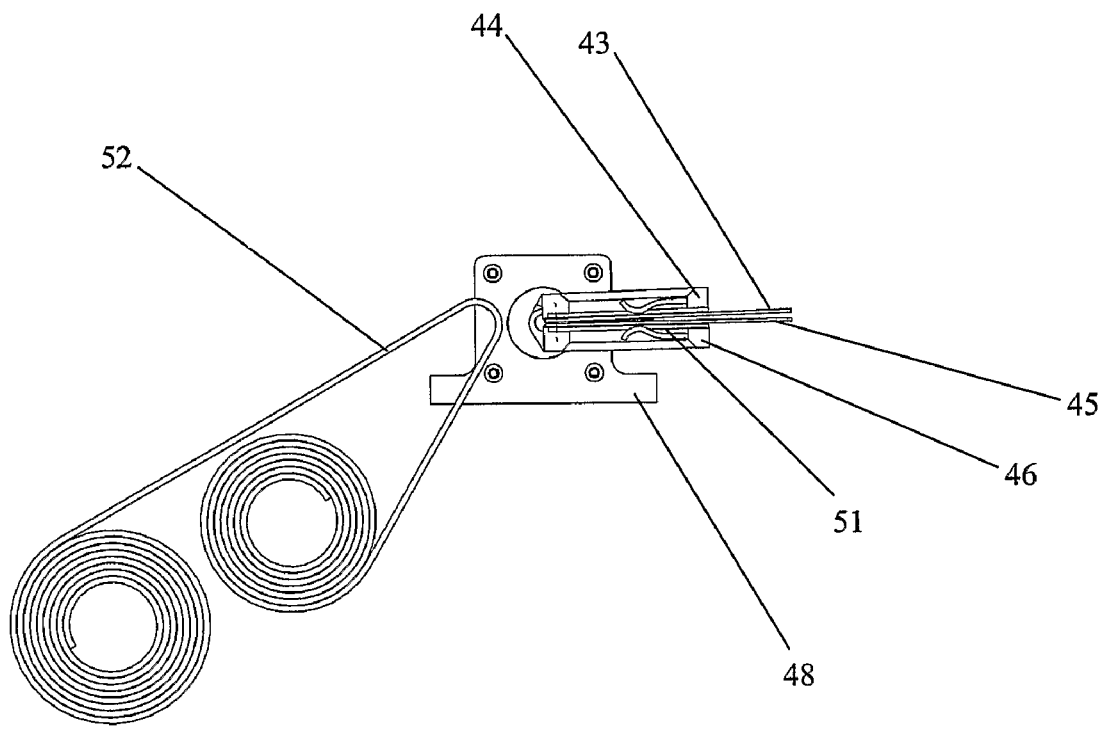

FIG. 14 is a depiction of a side view of a slide movement system in a closed position for the embodiment in FIG. 10.

Figure 15:
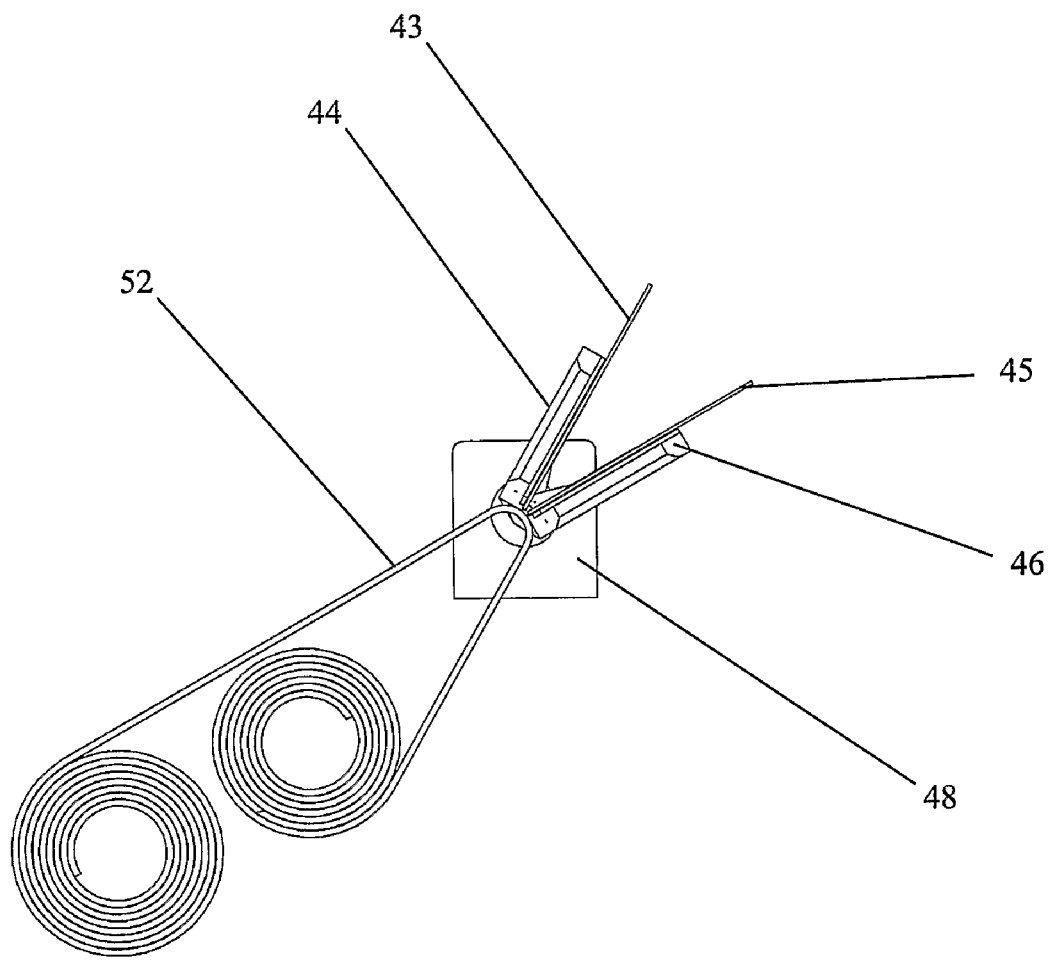

FIG. 15 is a depiction of a side view of a slide movement system in a tilted position for the embodiment in FIG. 10.

Figure 16:
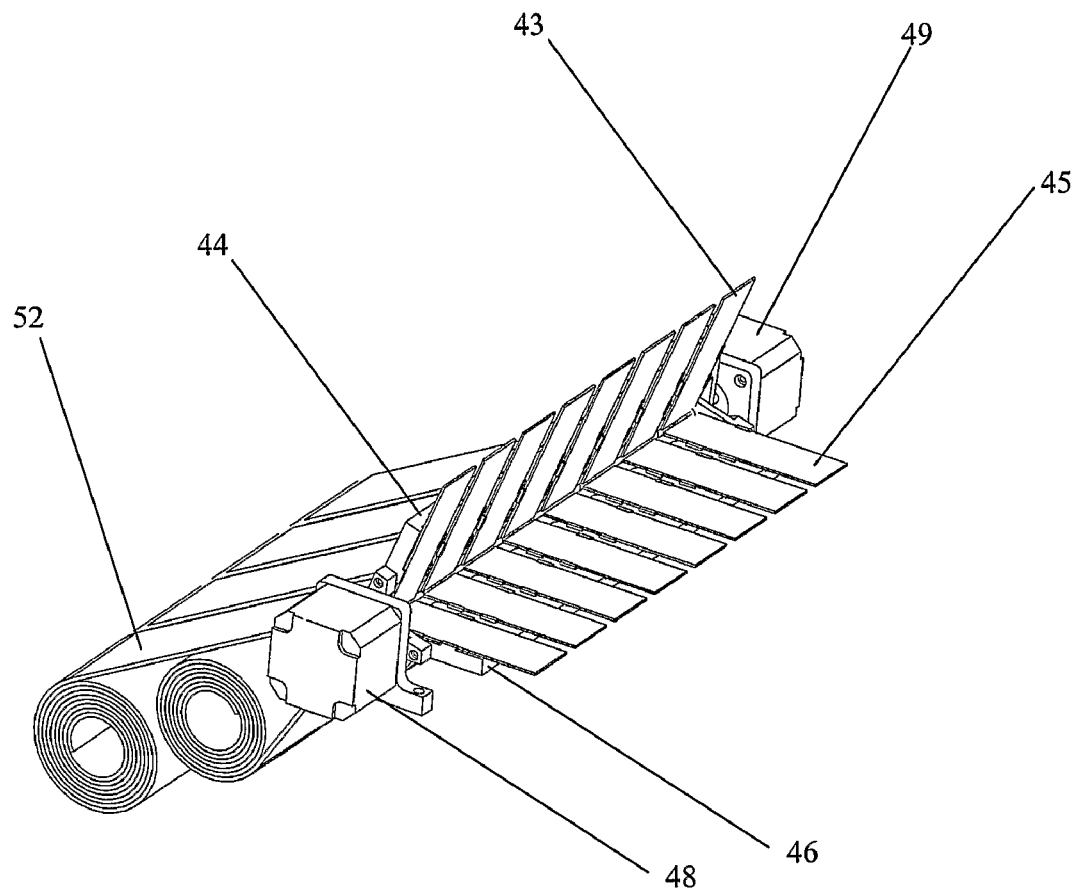

FIG. 16 is a depiction of a perspective view of a slide movement system in an open position for the embodiment in FIG. 10.

Figure 17:
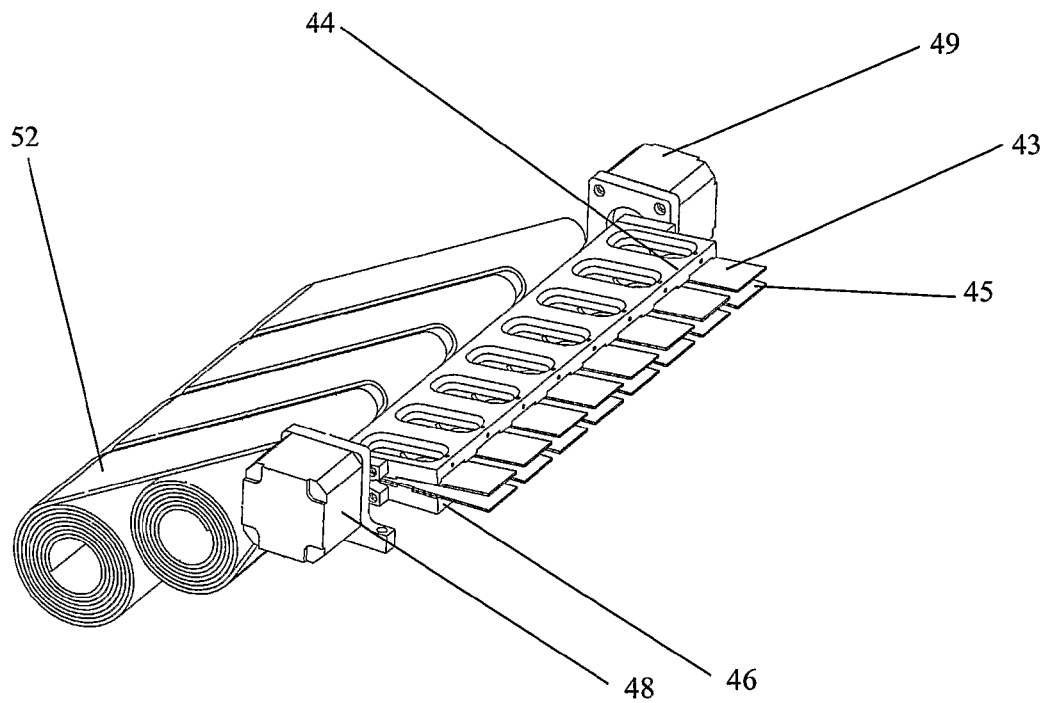

FIG. 17 is a depiction of a perspective view of a slide movement system in a closed position for the embodiment in FIG. 10.

Figure 18:
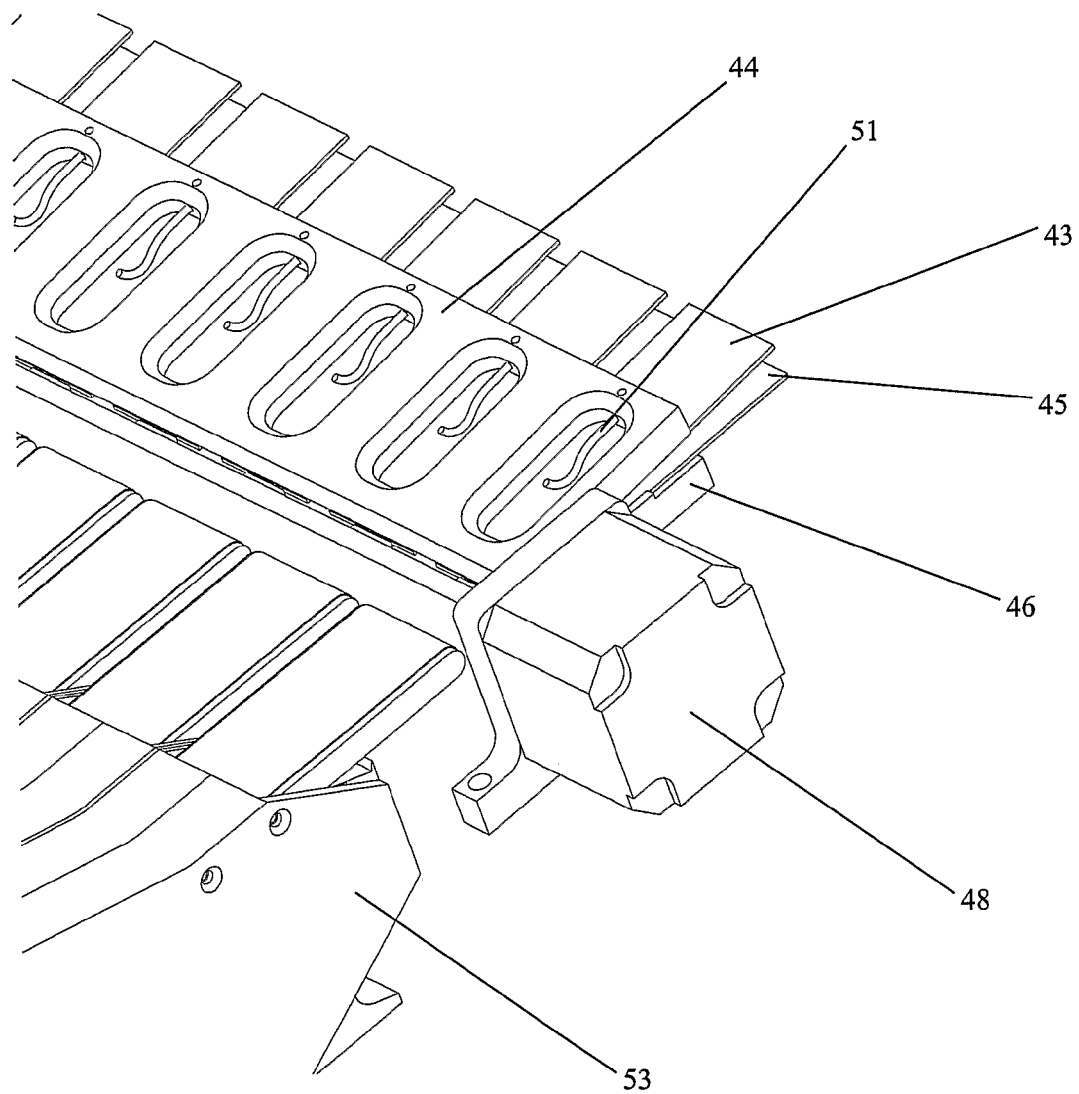

FIG. 18 is a depiction of a close up view a slide movement system in a closed position for the embodiment in FIG. 10.

Figure 19:
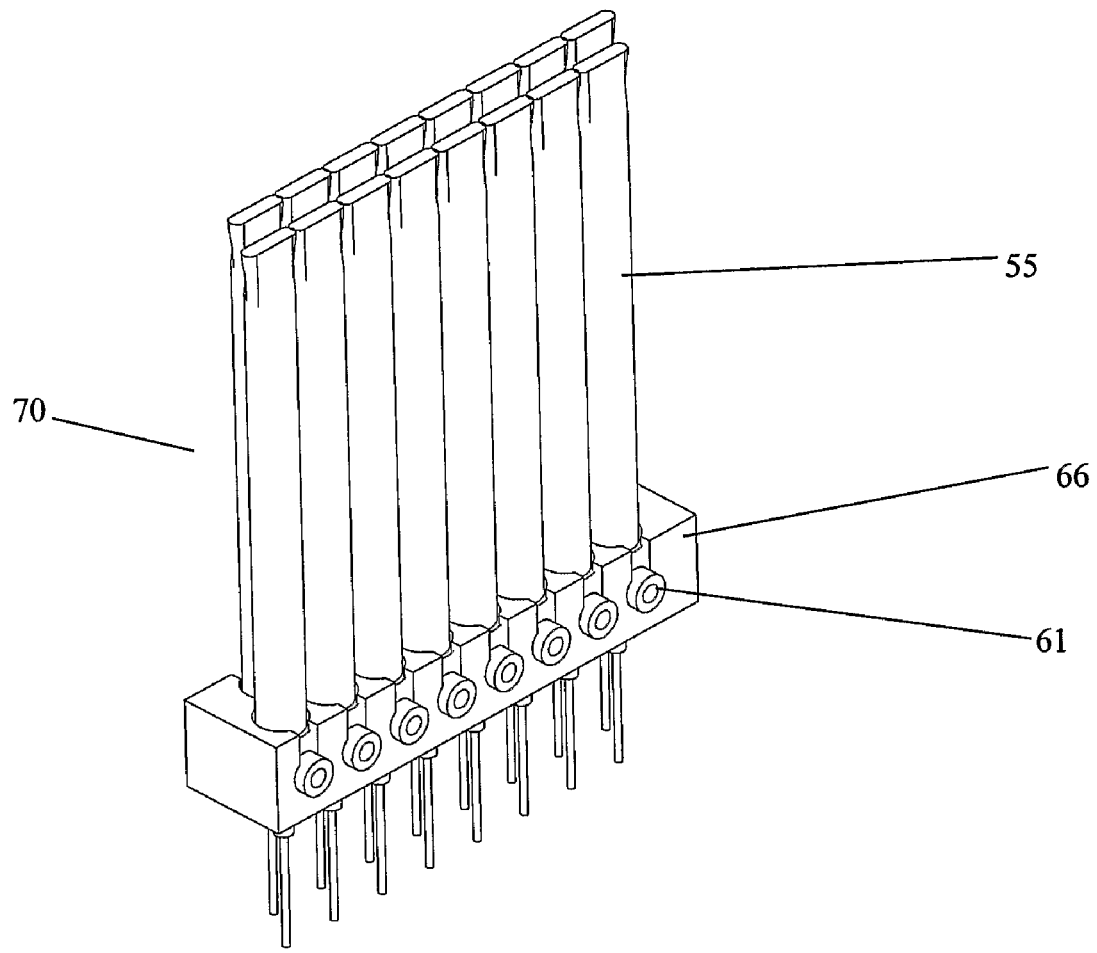

FIG. 19 is a depiction of a perspective view of one embodiment of a linear reagent magazine.

Figure 20:
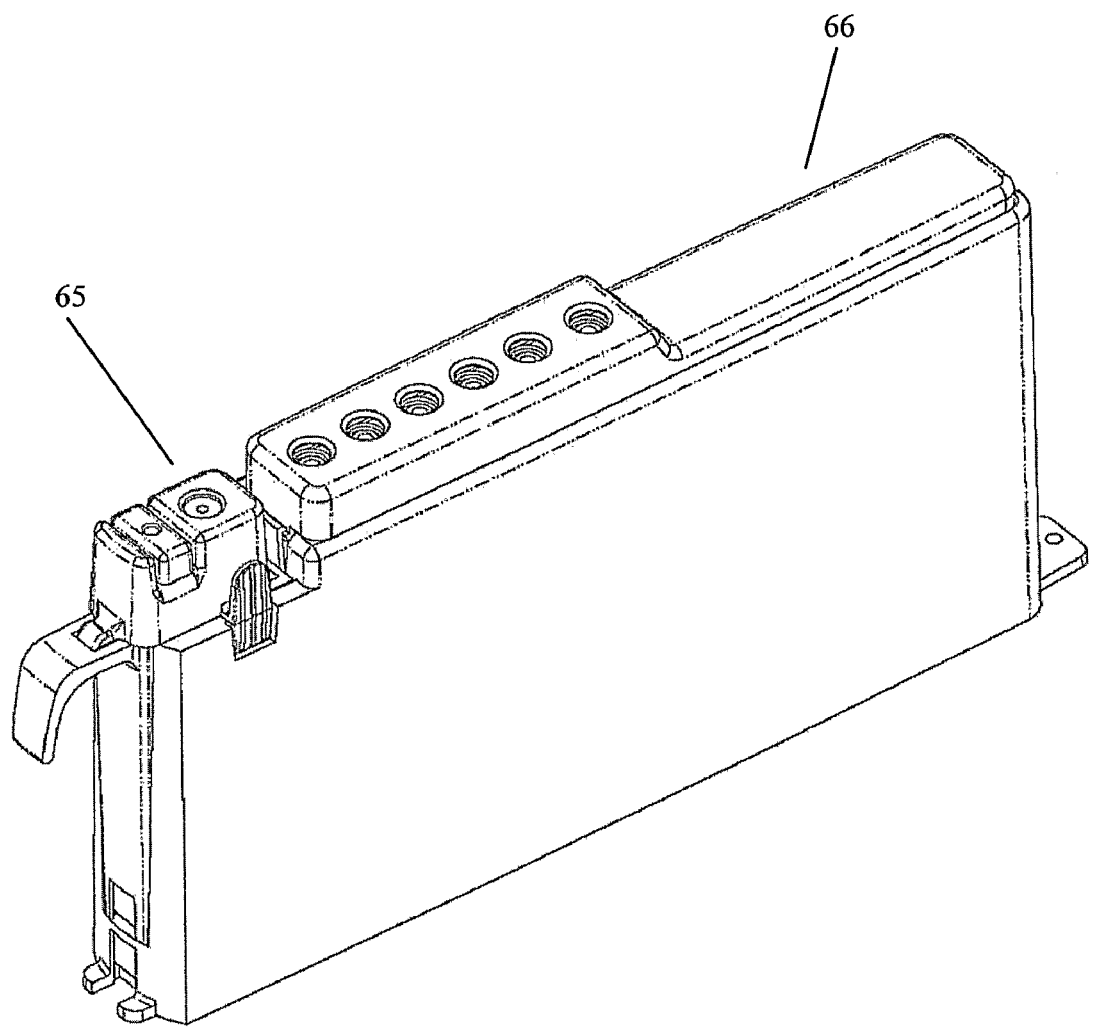

FIG. 20 is a depiction of a perspective view of a different embodiment of a linear reagent magazine with attached primary antibody cartridge.

Figure 21:
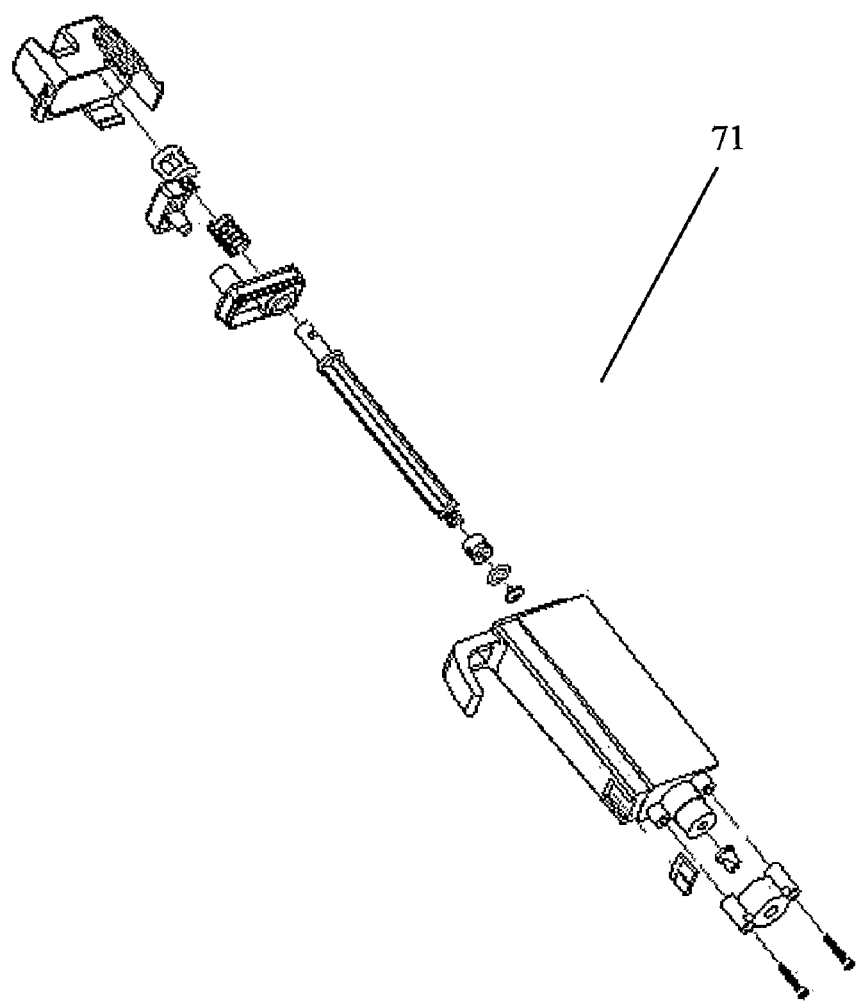

FIG. 21 is a depiction of an exploded view of an embodiment of a primary antibody cartridge.

Figure 22:
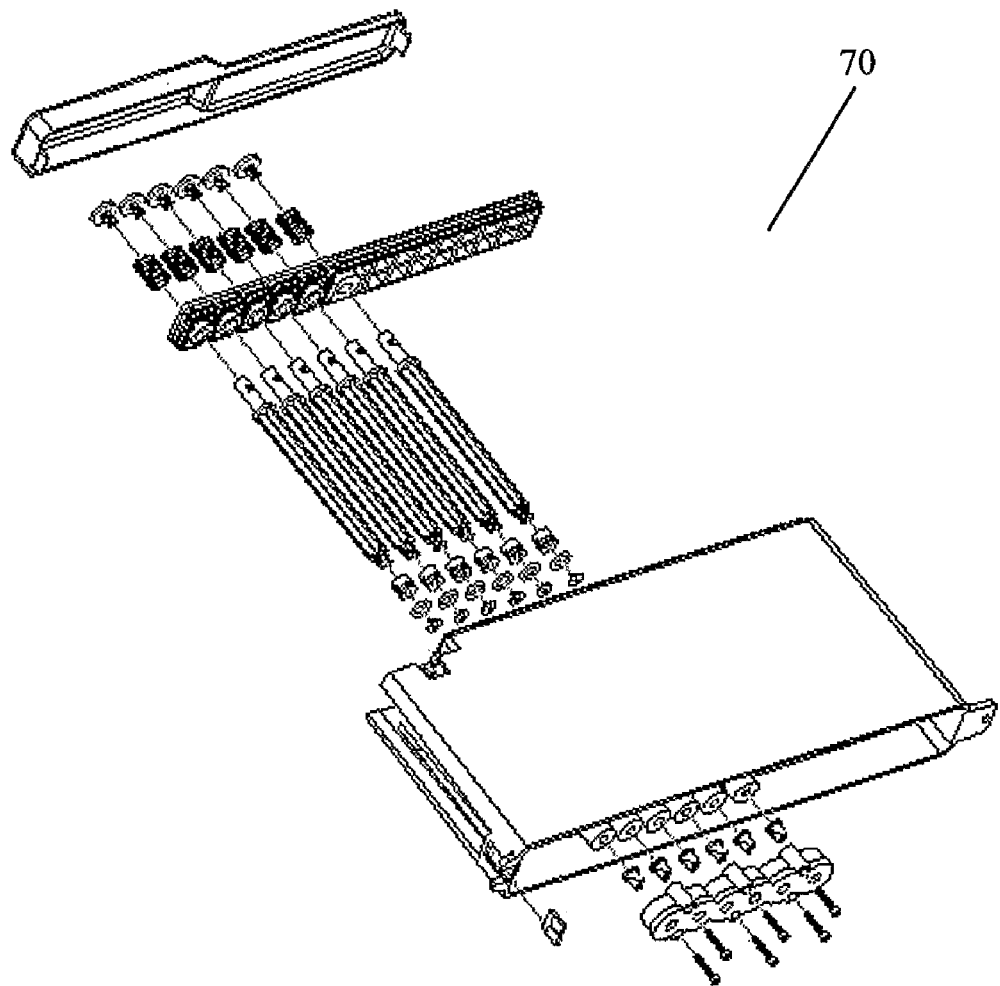

FIG. 22 is a depiction of an exploded view of an embodiment of a linear reagent magazine.

Figure 23:
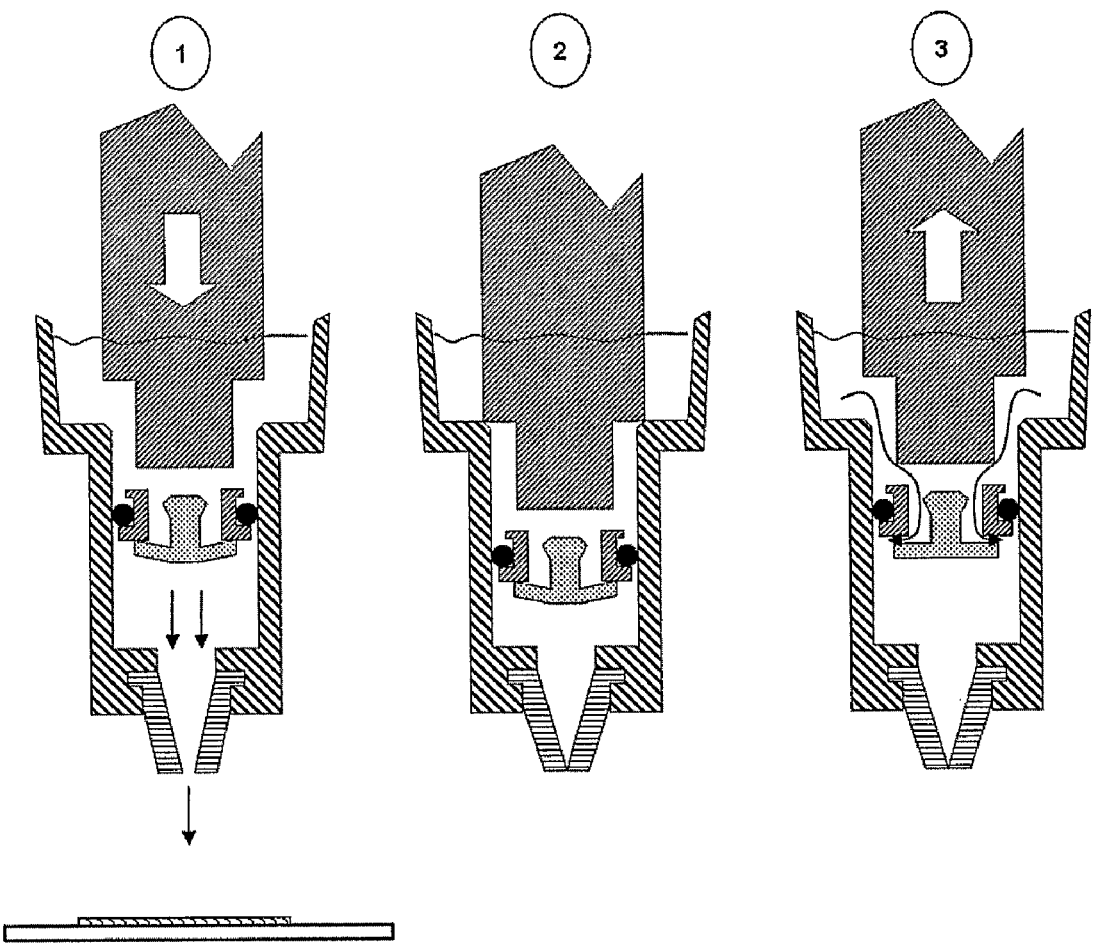

FIG. 23 is a depiction of the operation of an embodiment of a substance dispenser as may be included in either an antibody cartridge or a reagent magazine.

Figure 24:
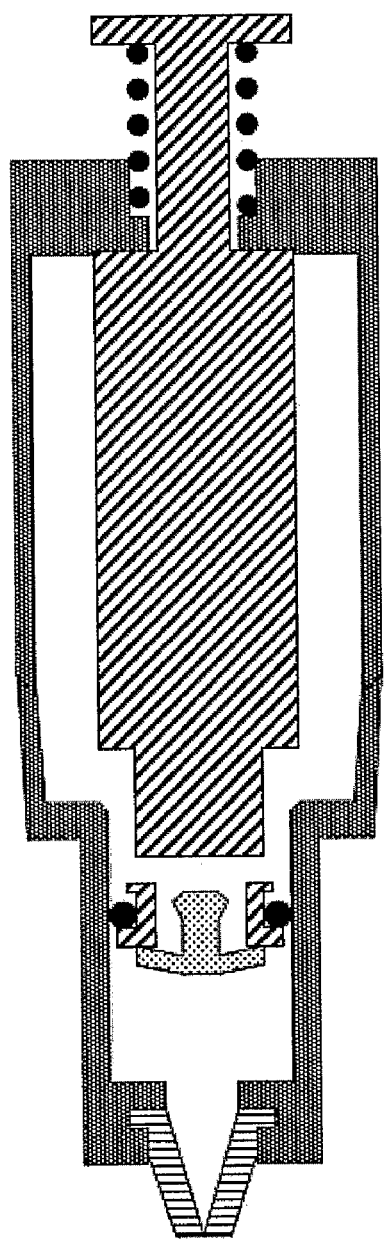

FIG. 24 is a depiction of a cut away view of an embodiment of a substance dispenser as may be included in either an antibody cartridge or a reagent magazine.

Figure 25:
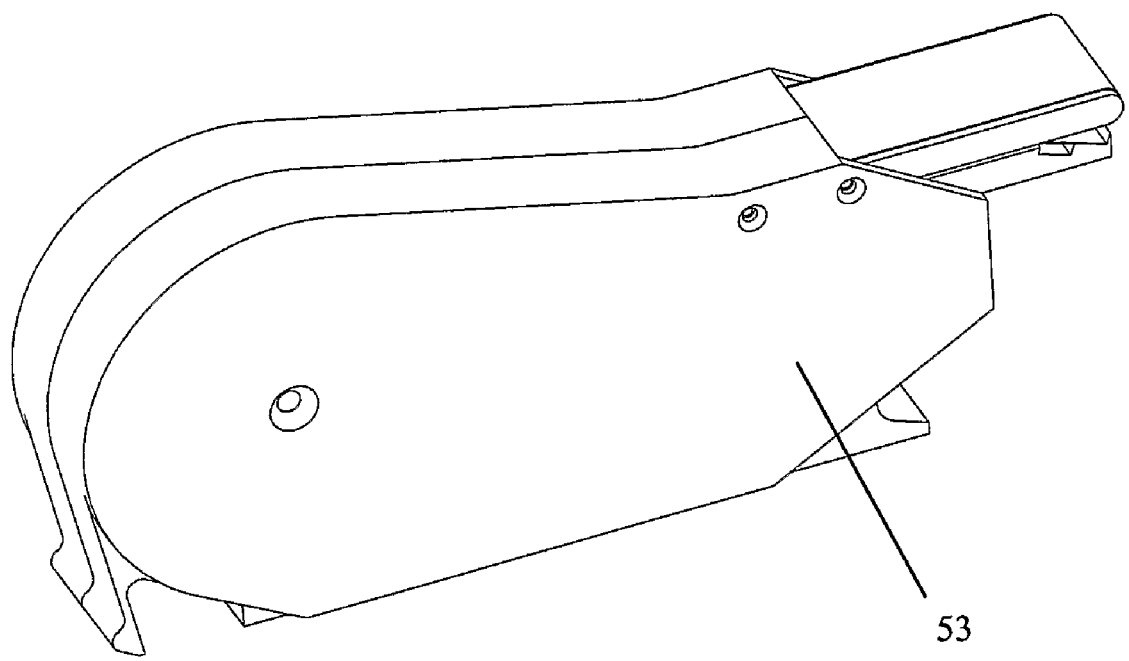

FIG. 25 is a depiction of a perspective view of one embodiment of a perpendicular wicking cassette.

Figure 26:
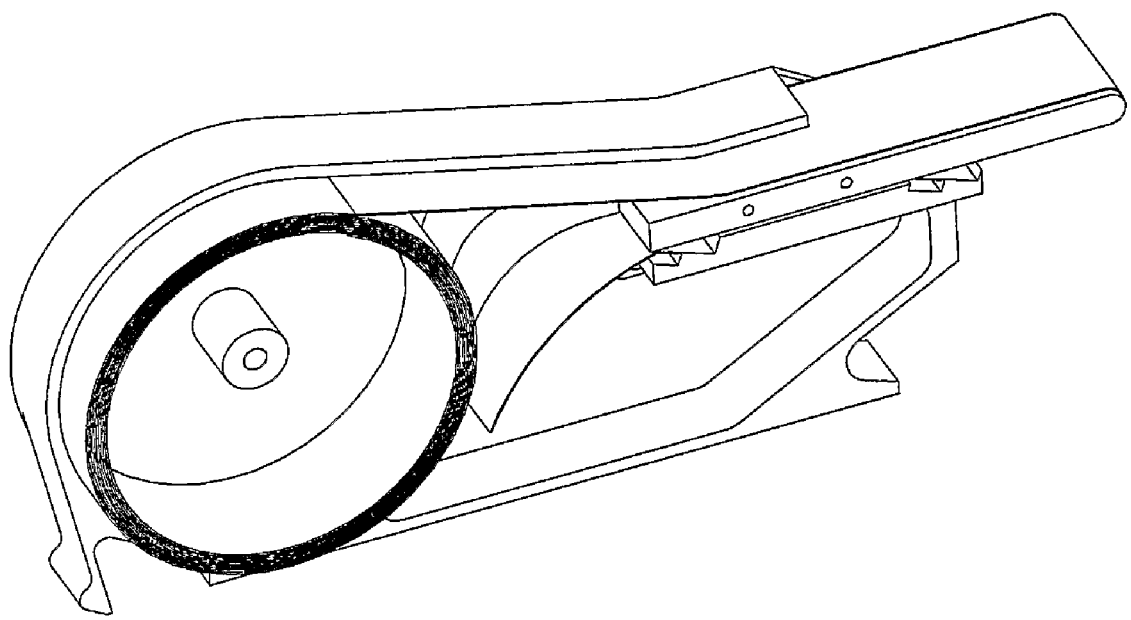

FIG. 26 is a depiction of a cutaway view of the embodiment of the perpendicular wicking cassette shown in FIG. 25.

Figure 27:
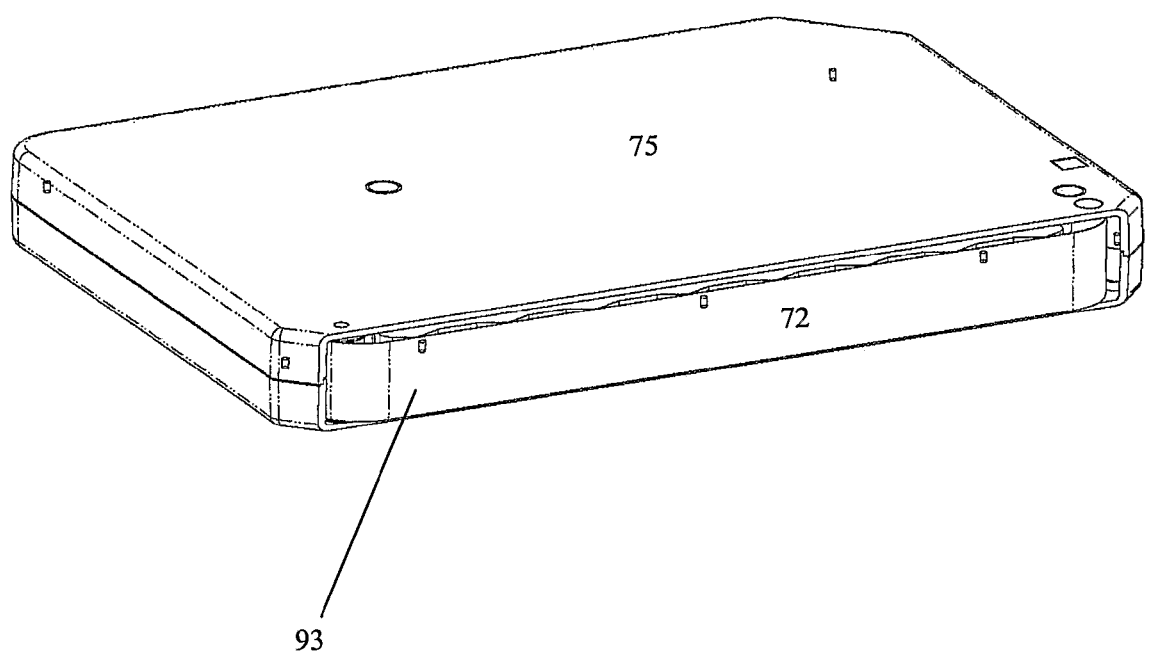

FIG. 27 is a depiction of a perspective view of one embodiment of a parallel wicking cassette.

Figure 28:
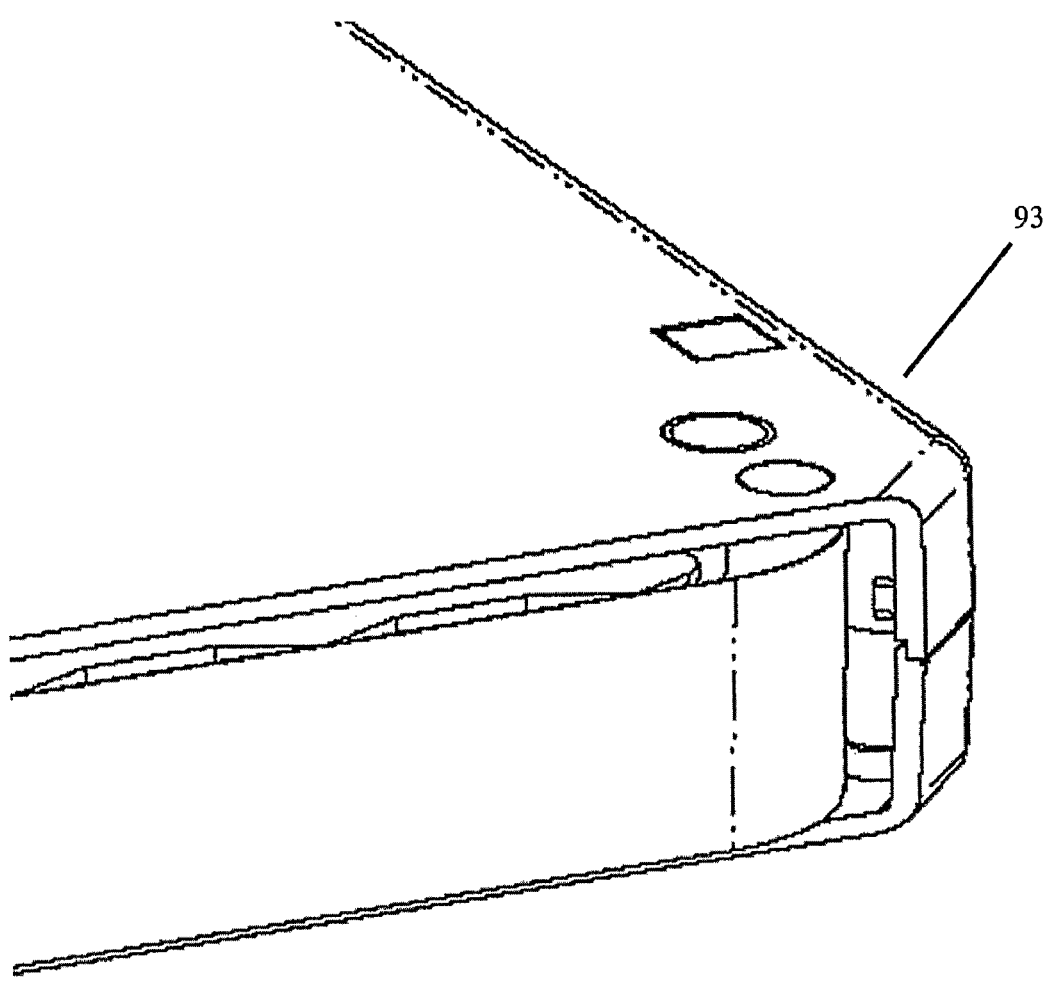

FIG. 28 is a depiction of a corner perspective view of the embodiment of the parallel wicking cassette shown in FIG. 27.

Figure 29:
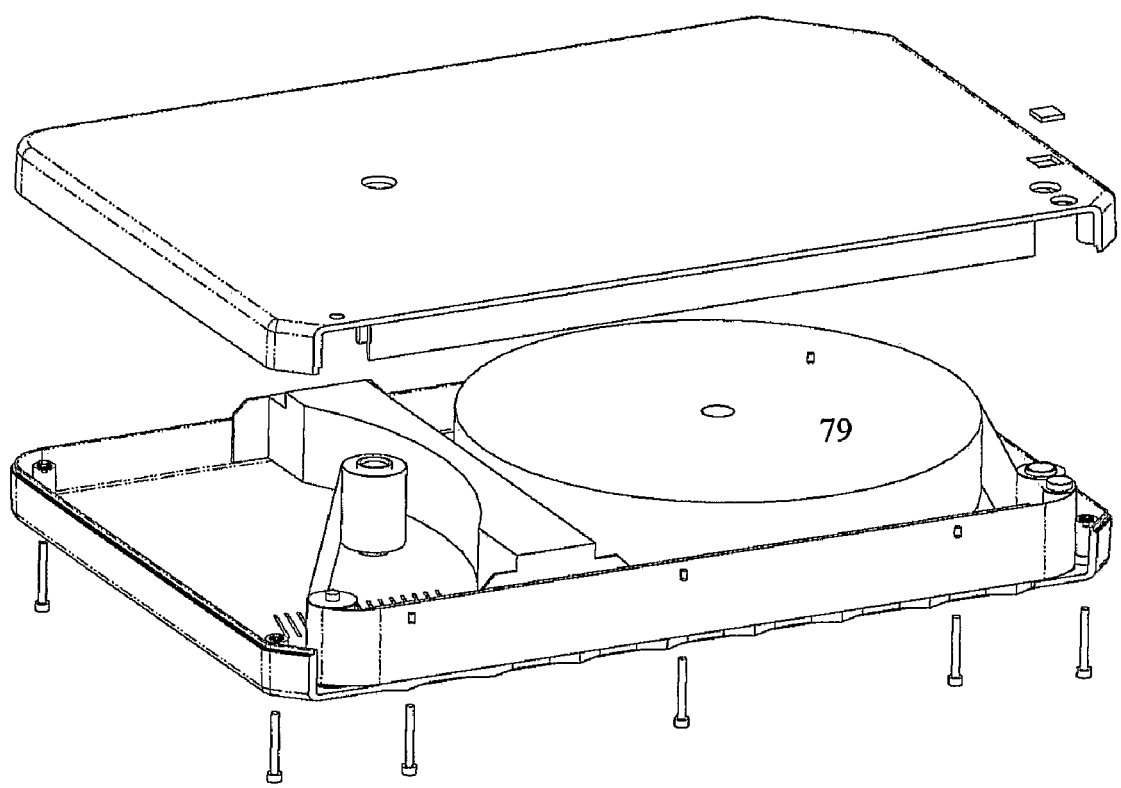

FIG. 29 is a depiction of a cutaway view of the embodiment of the parallel wicking cassette shown in FIG. 27.

Figure 30:
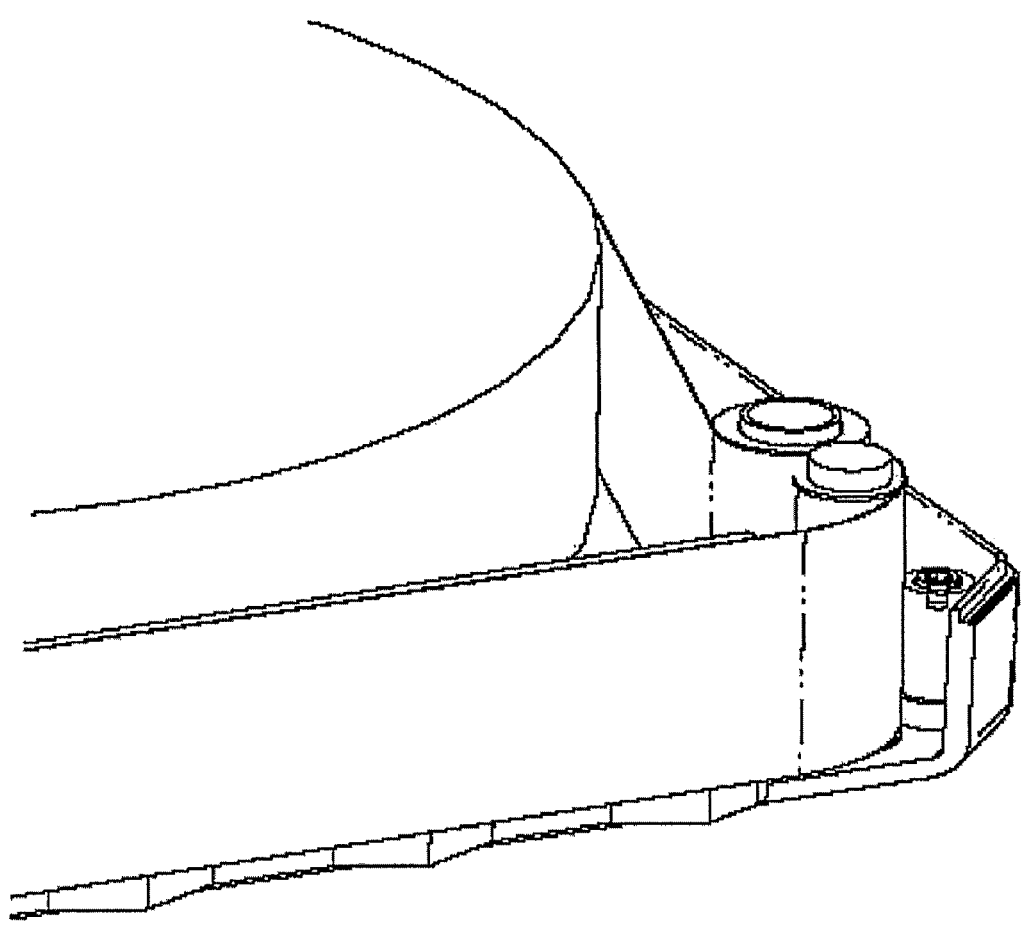

FIG. 30 is a depiction of a corner cutaway view of the embodiment of the parallel wicking cassette shown in FIG. 27.

5. MODES FOR CARRYING OUT THE INVENTION

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The present invention can be understood by reference to the detailed figures and description set forth herein. Embodiments of the invention are discussed below with reference to the Figures. However, those skilled in the art will readily appreciate that the detailed description given herein with respect to these figures is for explanatory purposes as the invention extends beyond these limited embodiments.

Referring to FIGS. 1, 2, and 10 through 19, it can be understood that embodiments of the invention may present a self contained system (56) perhaps with a system enclosure (60) that can achieve a method of rapid sample processing. In general, the system may involve obtaining a sample (1), placing that sample in a sample processing system (2), and then automatically processing that sample (1) by operation of the system. The system operator or other person can select an appropriate biochemical test sequence perhaps through a computer or perhaps touch screen display (57) or the like and the sample processing system (2) can be configured as or can include an automatically sequenced test processor (3). The system operator or other person can easily insert multiple reagent magazines and perhaps single primary antibody cartridges for the selected sequences. In embodiments, the sample processing system (2) can include an automatically sequenced biochemical test processor (3), an automatically sequenced histochemical test processor, an automatically sequenced cytochemical test processor, or the like so that it may act to accomplish a particular type of test not previously able to be accomplished in or perhaps merely desired to be accomplished in a rapid manner.

The sample processing system (2) can act to subject at least a portion of an exterior sample area (4) of the sample (1) to some appropriate interaction. By permitting this interaction, the sample processing system (2) may be configured to cause or to permit the placement of a substance (5) in the vicinity of the sample (1). Throughout the test sequence, substances are removed and held for disposal. As a result of the substance (5) placed on the sample (1), the sample processing system (2) can cause an appropriate interaction and thereby provide a detection indication. This detection indication may by caused by the presence of a specific type of biological substance within the sample (1). As mentioned above the sample processing system (2) can be used in even an operative environment. As such, it may be appropriate to make the sample (1) a thin biologic sample or the like. This sample may be placed on one or more thin biologic sample holders (6).

It may also be desired to accomplish a coincidental or parallel processing of a variety of samples at once. As such, the sample processing system (2) may have multiple sample holders. These sample holders may facilitate establishing a sample (1) on a surface (7). This surface (7) may be a substantially planar surface so that the sample is laid flat for easier interaction. In instances where the sample (1) is a thin biologic sample, the sample (1) may be placed on a slide such as a microscopic slide (8). In this instance, the sample processing system (2) may include a microscopic slide sample holder (9). A microscopic slide sample holder (9) may facilitate the placement of may aid in applying an appropriate substance (5) in the vicinity of at least a portion of an exterior sample area (4) of the sample (1). By establishing a sample (1) on a microscopic slide (8) traditional staining and analysis can be conducted, albeit in a shortened time frame.

With respect to coincidental processing, it should be understood that individualized biological samples may be run with disparate, sample specific biochemical test sequences. The automatically sequenced test processor (3) may act to automatically correlate a plurality of disparate, sample specific biochemical test sequences with individualized biological samples. Through this action the sample processing system (2) or perhaps the automatically sequenced test processor (3) may be considered as having a correlation element (67). By knowing which sample is on a particular sample holder, the system can assure that the proper sequence is run with proper sample.

Through not only the proper software or firmware but also appropriate hardware, the system can act automatically substantially coincidentally conduct at least a portion of biochemical test sequence. By substantially coincidentally conducting actions, the system can cause those actions to occur and nearly the same time for more than one sample. This may of course encompass all of biochemical test sequence. It may also, encompass specific aspects such as: subjecting a sample to a substance, incubating a sample in this substance, eliminating or perhaps transiently eliminating the substance, reapplying this substance, withdrawing a substance, and even achieving or accomplishing the ultimate desired results. Thus, by appropriate programming and perhaps use of appropriate mechanisms, the system can be considered as having a variety of substantially coincidental elements such as an: automatic substantially coincidental substance mixer, automatic substantially coincidental substance application element, automatic substantially coincidental paired sample substance application element, automatic substantially coincidental incubation element, automatic substantially coincidental substance transient elimination element, automatic substantially coincidental fluidic substance transient elimination element, automatic substantially coincidental capillary transient elimination element, automatic substantially coincidental substance reapplication element, automatic substantially coincidental substance withdrawal element, substantially coincidental automatically sequenced biochemical test processor, or the like. In instances where withdrawing a substance is accomplished by wicking, the system can be considered as having a substantially coincidentally wicking element and the like. This may be a capillary action substance withdrawal element when capillary action is used such as in a wicking situation. The system may be configured for fully coincidental actions as well. As can be understood from the figures, specifically considering FIG. 13 and the mechanical design presented whereby through a common hinged movement element (47), fully coincidental processing can be conducted for all the pairs of slides on that particular holder. Thus, by appropriate configuration, the plurality of samples can be configured for coincidental processing. Furthermore, the automatically sequenced test processor (3) AP configured as a fully coincidental automatically sequenced biochemical test processor.

As mentioned, at least a portion of an exterior sample area (4) of the sample (1) may be subjected to an appropriate substance (5). The substance (5) may be any appropriate reactive or even a non-reactive substance. To the presence of an appropriate interactive or perhaps reactive substance may facilitate actions so that detection can occur. In many instances, a substance (5) may be a fluidic substance (10). By subjecting the sample (1) to at least one fluidic substance (10) interaction such as antibody binding, staining, or the like may occur. Naturally, the fluidic substance (10) may be an appropriate reactive substance or perhaps an appropriate fluidic reactive substance. Thus, the sample processing system (2) may include some type of substance source, such as a fluidic substance source (11) as part of a preselected biochemical test sequence. The sample processing system (2) may also automatically cause actions such as by the fluidic substance source (11) that place fluidic substance (10) on a sample (1). In embodiments of the invention, this action may be conducted through the use of capillary action and thus a sample processing system (2) may capillarly subject a sample (1) to an appropriate substance (5). In some popular arrangements, the fluidic substance (10) may be a liquid substance. This liquid substance may of course be a solution, a suspension, or any other type of substance. In other embodiments, the invention can even be adapted to a nonliquid fluidic substance such as a gaseous substance.

Once the substance has been placed on a sample (1), the automatically sequenced test processor (3) may be programmed and may act to permit a sample (1) to be incubated in the presence of a substance (5). This programming may act as an incubation element (12) within the sample processing system (2). An automatically sequenced test processor (3) may act to accomplish the step of incubating the sample (1) in the substance (5) for some period of time after it also accomplishes the step of subjecting the sample of (1) to the substance (5). In some embodiments, the sample processing system (2) can accomplish incubation an unelevated temperature, such as room temperature or the like. Naturally, embodiments may act to heat the sample or the like and the temperature may actually be increased by some amount. For temperature sensitive substances, embodiments of the sample processing system (2) may not significantly externally heat the sample or the substance (5) and thus the sample processing system (2) may contain an unelevated temperature incubation element (13) by causing, whether through programming or the like, the sample (1) to incubate in the presence of a substance (5) without a significantly elevated temperature.

Of course, as the substance changes, the sample changes, or the process changes, the automatically sequenced test processor (3) within the sample processing system (2) may be differently programmed to utilize differing incubation periods for differing substances, differing samples, or the like. Depending upon the substance or samples involved, it is also possible for the automatically sequenced test processor (3) to even utilize no incubation period. This may be appropriate in instances where there is sufficient interaction in the time period where the substance (5) is placed and removed from a sample (1). It may also be appropriate for certain substances such as a buffer substance. In such instances, the buffer substance may be applied and relatively immediately removed with no significant incubation or delay period. By the term relatively immediately removed, it should be understood that while there may be pauses or the like that may be incidental to the mechanics or other processing aspects of the automatically sequenced test processor (3), no substantial delay may occur and thus no significant incubation period may exist for particular arrangements.

Naturally, the amount of incubation can vary. Significant in some embodiments of the present invention is the possibility that incubation can be greatly shortened as compared to prior techniques. Incubation may also be conducted in a sequence of partial incubation events. In some such partial incubation events it may be arranged such that the automatically sequenced test processor (3) may act to partially incubate a substance for less than or equal to a variety of times. These time may ranging from 90 seconds to zero seconds. Partial incubation events which may be such as 90, 60, 35, 30, 22, 20, 15, 10, 5, 3, and even zero seconds may be applied. In such events the sample (1) may also be subjected to the substance (5) without significant disturbance. In this undisturbed timeframe, an appropriate interaction, reaction, or other process can occur in a more traditional sense. In embodiments of the present invention, the amount of interaction can be far greater than would have normally occurred in the selected timeframe. Perhaps even more significantly, partial incubation can occur in time frames that are now dramatically shorter than previously understood as possible for the desired amount of interaction. Combining the partial incubation sequences, a total incubation time can thus be dramatically shortened. Again, through action of embodiments of the invention, the total incubation of a particular chosen substance can even be for a total time of less than or equal to about 300, 250, 200, 150, 20, 16, or even 10 seconds as part of a selected biochemical, histochemical, cytochemical, or other appropriate sample process.

At the end of specific substance portions of the test sequence, the particular substance involved is typically withdrawn from the sample. Especially when substances are reactive, this can present a hazardous material handling issue. Embodiments of the present invention can collect such spent substances in an enclosure for ultimate disposal. For overall simplicity and safety, snap in and snap out elements can be used to aid the operator.

Embodiments of the invention can act to greatly shorten the chemistry times previously thought by some to be unchangeable constants. Through appropriate programming, the automatically sequenced test processor (3) may act to initially permit an interaction between the sample (1) and an appropriate fluidic reactive substance. In situations as may be appropriate to many immunohistochemical tests, the system can be configured to permit a chemical interaction or even a chemical reaction to occur between the sample (1) and some substance such as an antibody substance (14) in a shortened time frame. These chemical interactions or perhaps reactions may take a variety of forms and may include interaction such as is present when an antibody binds to a particular cellular or other structure.

In embodiments of the invention, the system may be configured to act to confine and perhaps restrain the fluidic substance in the vicinity of a sample (1). This may create a bounded fluidic environment (15) or a restrictively confined fluidic environment (17). In some arrangements a sample processing system (2) may be configured so that it establishes a bounded fluidic environment (15) in the vicinity of the exterior sample area (4). This bounded fluidic environment (15) may be established through some type of fluidic boundary element (16). A fluidic boundary element (16) may actually be arranged and configured to permit the bounded fluidic environment (15) to exist in the vicinity of the sample (1). By acting to establish a bounded fluidic environment (15) in the vicinity of the exterior sample area (4), the system may serve to provide an environment within which an appropriate reactive substance (5) may be placed. Furthermore, the bounded fluidic environment (15) may serve a variety of purposes. First, it may act to limit the amount of fluidic substance (10) that is used from a source such as the fluidic substance source (11). This may serve to conserve what may prove to be a very expensive substance. In addition, the bounded fluidic environment (15) may serve to facilitate an appropriate action on the fluidic substance (10).

In embodiments, the bounded fluidic environment (15) may be configured to cause or permit a restrictively confined fluidic environment (17) in the vicinity of at least a portion of the sample (1). By presenting a restrictively confined fluidic environment (17), the sample processing system (2) may present a fluidic environment that enhances processing. In some embodiments a sample processing system (2) may include a multidirectional fluidic confinement element (18) that can act in more than one direction. It should be understood that this may not be merely a multidimensional confinement element, but rather multidirectional in that the directions may even be within the same dimensional context such as when binding on a top and a bottom, perhaps considered a single dimension, the Z-axis.

In some embodiments, the multidirectional fluidic confinement element (18) may actually be configured as an opposing surface multidirectional fluidic confinement element (19). This opposing surface multidirectional fluidic confinement element (19) may have two surfaces that oppose each other and thus confine a fluidic environment. In one embodiment, opposing microscopic slides (8) can be used to confine the fluidic environment. Had shown, configurations may arrange samples in opposing pairs. These opposing pairs made me think he adjacent opposing pairs as shown in a lined arrangement in the figures. As shown in FIG. 4, opposing microscopic slides (8) may act so that a small dimensioned area may be present between the two microscopic slide (8). In this one embodiment it can be understood how the restrictively confined fluidic environment (17) may serve to establish a multidirectional restrictively confined fluidic environment in the vicinity of at least a portion of an exterior sample area (4). By establishing an opposing surface multidirectional restrictively confined fluidic environment in the vicinity of at least a portion of the exterior sample area (4), that exterior sample area (4) may be preferentially subjected to an appropriate fluidic substance (10).

In some embodiments, the multidirectional fluidic confinement element (18) may be configured as an at least three directionally confined fluidic confinement element (20). This may be achieved through the use of an opposing surface multidirectional fluidic confinement element (19) such as shown with two microscopic slides (8) and an additional confinement direction, perhaps at the end of a microscopic slide (8) or at its label element or the like. Naturally additional directional confinement can be provided. Confinement can also be accomplished through the use of appropriate materials such as by using a hydrophobic material or the like. As but one example, it can be understood that by using a label that is hydrophobic, certain fluidic substances (10) may actually become confined in yet another direction. Confinement can cause at least three directions of confinement and thus can present an at least three directionally confined fluidic confinement element (20). Naturally it should be understood that a multidirectional fluidic confinement element (18) may act to establish a restrictively confined liquid environment or maybe even a restrictively confined gaseous environment.

As mentioned earlier, a variety of substances can be used in order to achieve the desired results. As such, a sample processing system (2) may include a substance source (21) that acts as a particular type of substance source. A great variety of substances can be used and thus the substance source can serve as a histochemical process substance source, a cytochemical process substance source, an organic substance source, a cytologic substance source, and even on a biomolecular substance source. Even with more specificity, a particular substance that is appropriate to particular tests can be used and thus a substance source can also have different types of substances including but not limited to reagents, primary antibody substances, and secondary antibody substances, chromogens, cellular substances, counterstains, histochemical probes, cellular substance counterstains, first chromogen components, second chromogen components, monovalent antibody substances, multivalent antibody substances, histologic substances, immunofluorescence substances, immuno gold substances, immuno gold silver enhanced substances, immuno cytochemical substances, immuno histochemical substances, fluorescent molecular substances, and even biologically specialized proteins. Further, substances produced by other substances can be used such as substances produced by antigen stimulation, substances produced by B-cell stimulation, B-cell stimulation produced proteins, immune response substances to other elements, immune responses to antigens, immunoglobulins, and otherwise. Of course, a variety of stain substances can be used such as basophilic stains, acidophilic stains, hematoxylin stains, eosin stains, eosinophilic stains, H&E stains, Lee's stain substances, Mallory's connective tissue stain substances, periodic acid-Schiff stain substances, phosphotungstic acid hematoxylin stain substances, silver stain substances, Sudan stain substances, Wright's stain substances, Verhoeff stain substances, trichrome stain substances, geimsa stain substances, tristologic substances, cytologic substances, biomolecular substances, and even substances that contains any combinations of the above. As should be understood, a substance source (21) may be part of a system that includes an appropriate substance type of processor (22). In this fashion the system may include a histochemical processor, a cytochemical processor, or the like. Furthermore the system can be configured to subject the sample to any of these substances.

An important aspect of embodiments of the present invention may be its use with particularly challenging substances such as low affinity antibody substances or perhaps low temperature antibody substances. In this manner, embodiments of the invention can serve to achieve results where previously they may not have been practically possible. As one example, a low affinity antibody substance, such as any antibody substance that typically does not exhibit an acceptable percentage of binding within the previously understood time frames, can be used. As such, the sample processing system (2) may serve through its programming or the like to subjects the sample (1) to a low affinity antibody substance. A type of low affinity antibody substance may even be a substance that has not previously been effectively usable in automated staining devices. In addition to low affinity antibody substances, a heat sensitive antibody substance might also be used. While in some systems such antibody substances may not have been used in the past, now they might be used to a greater degree. While some systems utilized heat to cause accelerated interaction within the previously acceptable time frames, the present system may be able to be used with anybody substances that are heat sensitive. Thus some substances that may not have been able to be used may now be usable. This may exist even if the accelerated time frames are not available due to their intolerance to elevated temperatures and their low affinities. In some instances, an antibody that typically and traditionally bound less than about half of its typical eventual amount in about 150, 180, or 240 seconds might be used. All this, of course, may even take place under normal temperature conditions and thus the system may be used with an antibody substance that traditionally takes longer than the mentioned time frames to bind about one half of their typical eventual amount under normal temperature conditions.

As mentioned earlier, a sample processing system (2) can act to facilitate accomplishing a variety of different test sequences or test processes. Applying embodiments that permit rapid processing, the system may be configured to accomplish rapid immunohistochemistry, immunocytochemistry, in situ hybridization, fluorescent in situ hybridization, chromosomal identification, staining, antigen retrieval, cytochemical, molecular chemical, epitope retrieval, or even pretreatment processes. These different types of processes can also be applied to a great variety of samples. Thus by obtaining a particular type of sample and perhaps placing that sample in a sample holder—perhaps such as a microscopic slide sample holder (9)—the sample processor or perhaps the automatically sequenced test processor (3) can be configured to process a variety of differing samples. These can samples can be biologic, cellular, tissue, biopsy, carcinoma related, melanoma related, lymphoma related, margin testing related, epithelial cell, lymph node, undifferentiated tumor cell, pediatric cell, mohs mapping cells, h.pylori cells, an chronic villi tissue cells, neonatal herpes cells, proteomics cells, or other types of samples. As such, the processor can be any one of these types of processors through appropriate programming to achieve a test and act on samples of the type mentioned. The entire sample processing system (2) can provide a detection indication of the presence of some type of biological substance within the sample (1). This detection, may include a detection indication of the presence of a carcinomic, tumor, phagocytic, lymph node, transplant procedure, tumor differentiation, pediatric pathology, mohs mapping, margin, margin indicative, h.pylori diagnosis, therapeutic marker, chronic villi tissue, neonatal herpes, virally, bacterially, infectious diagnostic, or just a molecular indicative type of substance within the sample.

A specifically important type of processing may be immunohistochemistry processing. As such, the sample processing system (2) may accomplish any one of the particular types of processes involved in immunohistochemistry. It may include an appropriate type of immunohistochemistry processor. When such a processor is appropriately configured, it may serve as an automatically sequenced test processor (3) and may be of any type mentioned. In general, biochemical processing may include a great variety of types of chemical processing including but not limited to histochemical processing, cytochemical processing, immunohistochemical processing, and the like.

In some embodiments, a significant aspect may be the fact that the present invention can be configured to achieve rapid biochemical processing. As such, the sample processing system (2) may include a fast biochemical sample processor (24). This fast biochemical sample processor (24) can act to accomplish the desired results and accomplish a completion time that is shorter than a traditional completion time period. The traditional completion time can be considered as the time at which is presently understood as being the amount of time necessary in order to achieve desired results for a given type of sample, given type of process, given type of test apparatus, and/or a given type of substance. For the same type of configurations, the present invention can achieve fast biochemical processing through the use of a fast biochemical sample processor (24) which may be configured to achieve the same desired results as might normally be chemically expected in longer time period. A fast biochemical sample processor (24) may act in less than a traditional completion time to achieve the same desired results. In some embodiments this may be achieved without elevated temperatures and thus the system may act on an antibody substance to be in less than a traditional unelevated temperature binding time period.

As a fast biochemical sample processor (24) the system may be configured to automatically achieve the biochemical test sequence in less than the traditional completion time while still achieving the same desired results. This may even be an intentionally shortened reaction period in which the substance (5) may interact with the sample (1). In such a configuration a fast biochemical sample processor (24) may even act as a biochemically time shortened interaction element. This may serve as a reduced detection time period process completion element. Embodiments may provide a detection indication in a reduced detection time period so that it can be used in an intraoperative or other shortened time environment. Naturally by presenting a method of rapid biochemical processing it is possible that the present system may be used beyond environments that merely require shortened processing. It may also be used in instances where it is desirable to simply take less time. In instances where antibody substances are used to bind with a sample (1), a system may be configured to subject a sample to a reduced antibody binding time period. This may be achieved by enhancing the interaction substantially along at least a portion of a bounded fluidic environment (15). It may of course also occur within a restrictively confined fluidic environment (17).

By allowing enhanced interaction to occur for at least some period of time, embodiments of the invention may permit rapid biochemical processing. It should be understood that this rapid processing can merely be something that is shorter than a recommended reaction period. The interaction need only occur in some shortened time frame as compared to that traditionally accepted for a particular situation. Embodiments of the sample processing system (2) may have reduced times as compared to a traditional interaction, completion, reaction, or detection time frame for a given situation. Perhaps surprisingly the present invention can achieve an acceptable level of interaction or reaction in less than an anticipated to timeframe. Thus, although desired results were typically not chemically expected until in longer time period, the present invention can present those same results in a shortened timeframe. This shortened timeframe may even be a less than a recommended reaction period and it may also be conducted as part of a simple automated biochemical test sequence.

By limiting a period within which an appropriate reactive substance may substantially be reacted, the present invention can serve to achieve rapid results, namely, results in less than a traditional completion time period. This timeframe may be an intentionally shortened reaction period. Embodiments of the invention made provide a detection indication in the presence of the specific type of biological substance in a reduced detection time period and may utilize a reduced reaction time period element, a reduced interaction time period element, or perhaps a reduced binding time period interaction element (25). This reduced time period interaction element (25) may be programming such as contained within an automatically sequenced test processor (3) in the sample processing system (2) or it may be present as hardware or firmware. The reduced time process completion may be a reduced time process completion element (26) and may be included in the sample processing system (2) as well as a reduced detection time period process completion element. By utilizing a reduced time period in whatever context, embodiments of the present invention can achieve the results even perhaps with unelevated temperature conditions. Thus, embodiments of the invention may utilize a reduced unelevated temperature interaction time period for a particular substance.

In some embodiments, the amount of interaction may be an appropriate amount. In situations such as the binding of an antibody to a sample (1), embodiments of the invention may accomplish a significant percentage of a traditionally accepted total amount of unelevated temperature antibody binding in a reduced time period. These significant percentages may be percentages such as greater than or equal to about 70, 80, 90, 95, 98, perhaps substantially all, or even 100% of a traditionally accepted total amount of unelevated temperature antibody binding. A qualitative amount and time frame can also be provided such as embodiments which provide a detection indication in less than or equal to about a visiting outpatient, an intraoperative procedure time limit, or perhaps even the College of American Pathologists Intraoperative Guideline amount of times. By achieving results in these more general contexts, the present invention can offer systems that can be used more effectively by doctors and more effectively for patients. The present invention may thus be appropriate for use in an operating room time constraint environment or the like. It may even permit use in a surgery time constraint environment or the like. Quantitatively, embodiments of the invention may provide a detection indication in less than about the aforementioned 60, 45, 30, 20, 15, 12, and even 10 minute time frames. Aspects of the system such as the automatically sequenced test processor (3) a such may be configured to serve as a reduced histochemical detection time period process completion element. These may be configured to provide a detection indication in less than any of the previously mentioned time frames. A system may also be configured to use interaction times that are less than about 75%, 50%, 30%, 23%, or even 18% of a traditional unelevated temperature interaction time frame. This may also apply in situations with elevated temperatures as well. A system may also provide a completion element configured to provide the aforementioned detection indication time frames and made provide a histochemically time shortened interaction element with the aforementioned time frames. As mentioned earlier, the system may provide an indication in less than or equal to about 500, 400, 300, 240, 180, 150, or perhaps even less than or equal to about 120 seconds times. This may occur for substances that cause about 50% or perhaps 80% of their traditionally accepted total amount of unelevated temperature interaction in longer than about 90 for the 50% amount or perhaps 660 seconds for the 80% amount.

In order to achieve a shortened timeframe or interaction aspects, the system may include activities that cause a forced action within a fluidic environment. The system may act to apply a motive force in the vicinity of the sample. This may occur through a motive force element (23). This motive force may be applied substantially along at least a portion of the restrictively confined fluidic environment (17). By automatically applying a motive force, the automatically sequenced test processor (3) may act at appropriate times. This application of a motive force may, in some embodiments, initiate a fluid wave. By affirmatively initiating a fluid wave, fluid within the restrictively confined fluidic environment (17) may be moved. The affirmative initiation of a fluid wave may also occur in a restrictively confined fluidic environment (17). All this may occur at time when the fluid needs or will be enhanced by being replenished in some fashion.

In some embodiments the automatically sequenced test processor (3) may act to affirmatively initiate an oscillatory fluid wave, that is, a fluid wave that may occur and move back-and-forth multiple times. These may or may not be of a regular nature and may or may not have pauses in between. Through such a program, the system to include subroutines or the like that may serve as an oscillatory fluid wave element (27). Naturally, it should be understood that the oscillatory fluid wave element (27) need not be included. In some embodiments the system may include a general fluid wave element. This fluid wave element may merely cause some sort of fluid wave to occur within a bounded fluidic environment (16) for at least some period of time period. A fluid wave element may act within an area such as the restrictively confined fluidic environment (17), and thus the system may cause fluid motion in this environment. As explained later, in some embodiments this might remove a fluid from the fluidic environment and then may even reapply the fluid to that fluidic environment. The system may also act to automatically substantially stop the fluid wave such as by removing the motive force that causes the wave in the first place.

Figure 1:
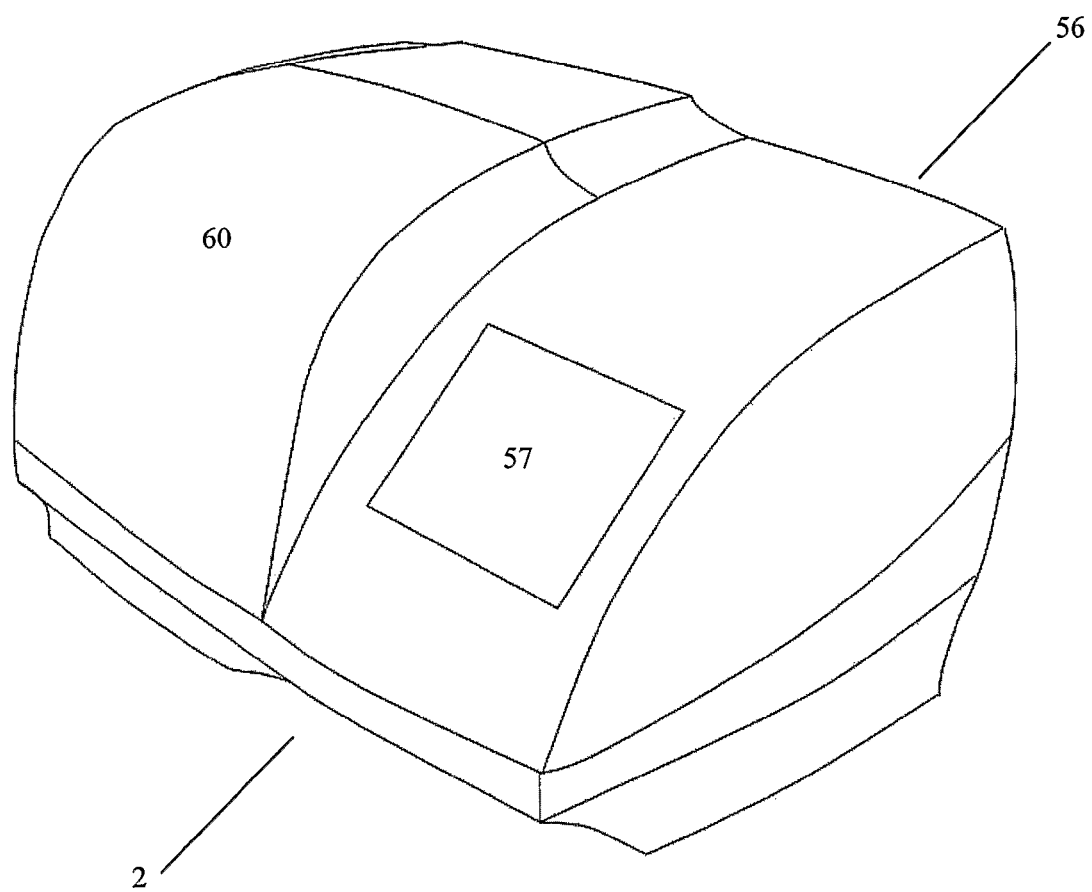
FIG. 1 shows a depiction of outer view of a self contained system according to one embodiment of the invention.
Figure 2:
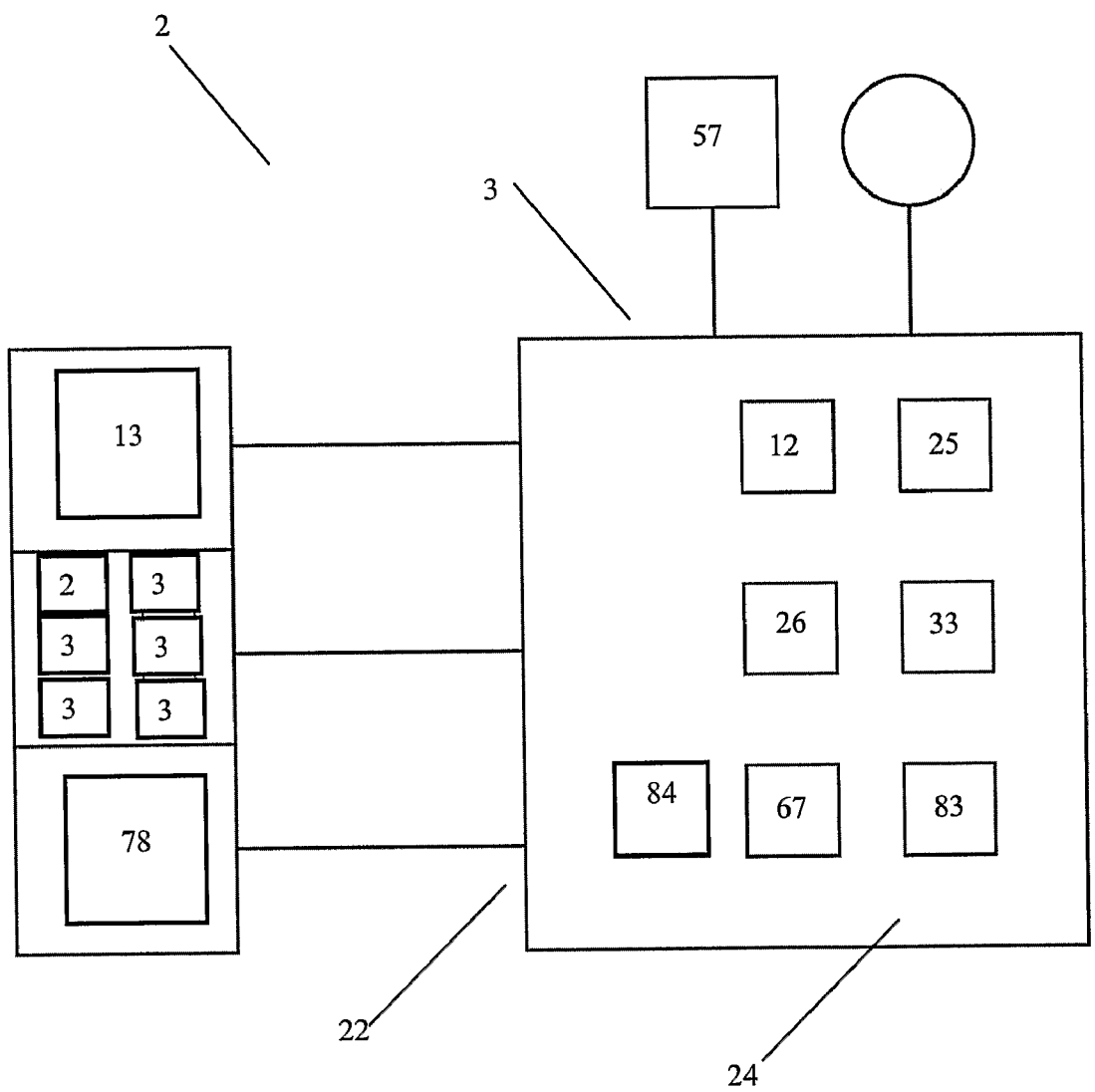
FIG. 2 is a conceptual schematic depiction of one embodiment of a sample processing system.
Figure 3:
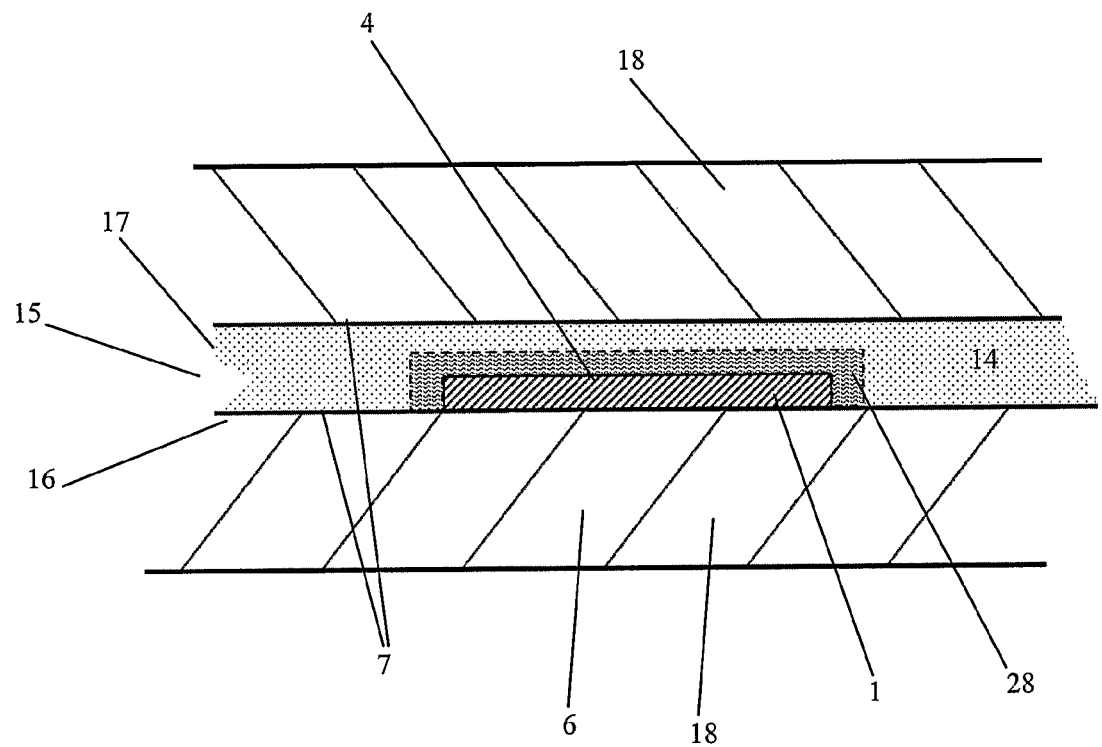
FIG. 3 is a depiction of an enlarged view of a bounded fluidic environment such as in between two slides.
Figure 4A:
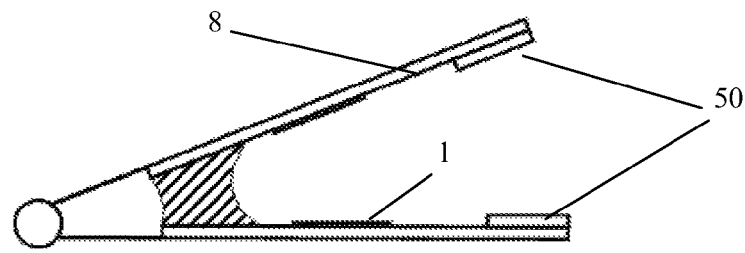
Figure 4B:
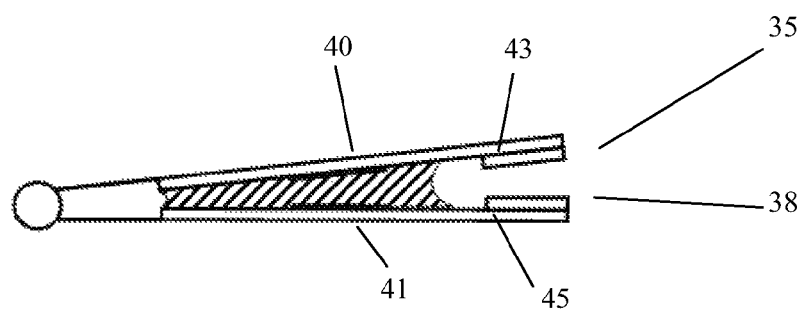
Figure 4C:
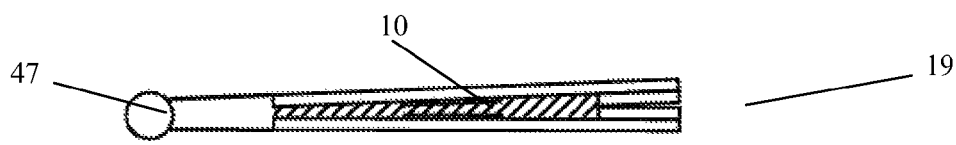
Figure 4D:
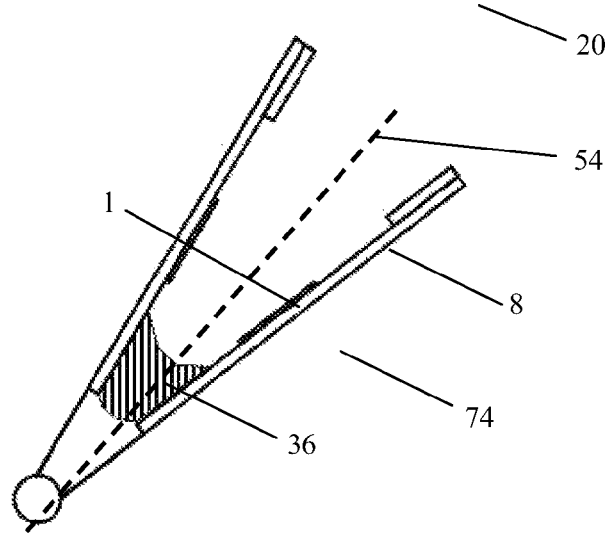

As mentioned earlier, one of the aspects of an embodiment of the invention may counter a depletion of a substance (5) as it interacts with the sample (1). As shown in FIG. 3, a sample can be subjected to the substance (5) through some type of fluidic environment. This fluidic environment may be a restrictively confined fluidic environment (17). Within any type of fluidic environment, restricted or not, there may be contained a microenvironment (28) which may exist immediately next to the sample (1). This microenvironment (28) may also be immediately adjacent or next to the sample (1). A microenvironment many contain elements of the substance (5) which actually interact with the sample (1). When elements of substance (5) become depleted, the amount of interaction may slow down. An aspect of embodiments of the present invention may be the fact that this microenvironment (28) can be replenished without replacing the entire fluid. Specifically, as can be understood from FIG. 4, by eliminating the fluidic substance (1) from within the microenvironment (28), the fluidic substance source (11) can be replenished and subsequently replaced. Through appropriate arrangements, the sample processing system (2) can include a sample interface microenvironment affirmative depletion avoidance element (29). This sample interface microenvironment affirmative depletion avoidance element (29) may be a combination of programming and perhaps hardware that acts to achieve the appropriate activity. This action may be as simple as merely accomplishing substantial mixing within the sample interface microenvironment (29). Interestingly, while air knifes and the like have been used, these appear to have not achieved the level of mixing necessary in the microenvironment (28) in order to afford substantially reduced process times as embodiments of the present invention can now achieve. In fact, existing systems (which may even use air knife systems) still retain the old processing times of an hour or perhaps even 90 or 120 minutes whereas the present invention affords significantly shorter process times—times that are less than an intraoperative 20 minute guideline.

To minimize substance usage, and to efficiently achieve the goal of rapid processing, embodiments of the invention can act to non-replacingly substantially refresh the substance (1) in the microenvironment (28) adjacent the sample (1). This can occur in the sample interface microenvironment, by acting to transiently eliminate the substance (5) from within the vicinity of the sample (1) and then acting to reapply that same substance. As mentioned, substantial refreshing can occur. Even in other systems that move a fluidic substance (10), such does not appear to occur as evidence by the fact that even those systems still have the slow process times and do not act to rapidly process the sample as in embodiments of the present invention. As shown in FIG. 4, this can occur by moving the perhaps firm surfaces (7) that define the bounded fluidic environment (15) or perhaps a firmly restrictively confined fluidic environment. By the term firm, it should be understood to encompass both rigid or even pliable boundary elements. It can also occur by taking advantage of the effects of capillary action as shown. Through such activity, the sample processing system (2) or perhaps the automatically sequenced test processor (3) through the inclusion of a subroutine or programming or the like can be considered as having a sample interface microenvironment substance refresher element (30). This can achieve refreshing the fluidic substance (10) without replacing it.

Chemically, by refreshing the substance a high level of the desired activity can continually occur. As shown in FIG. 5 with respect to a representative substance, in this can a particular antibody substance, this can be understood. In this graphic depiction of what a traditional accelerated/heated antibody substance binding profile may be like (58), slow binding activity may likely be due to depletion of the antibody substance in the microenvironment (28). Thus the typical binding of an antibody substance can take in excess of 14 minutes to achieve 95% of its eventual amount of binding. By acting, perhaps through the five waves or the like as shown to repeatedly refresh the substance (5), embodiments of the system can achieve the refreshed antibody substance binding profile (59) shown. Through this refreshing, the curve can be repeatedly on its steeper portion and thus a higher rate of binding or other interaction can be achieved.

To achieve this transiently, such as in where the substance (5) is available for reapplication at some later point in time, embodiments of the system can establish a collected fluidic substance (36) as shown. Elimination of the substance (5) can also be substantial in that most is removed even though some perhaps slight amounts may remain on or in the vicinity of the sample (1) or the surface (7). It should also be noted that eliminating the substance (5) from the sample (1) is not the same action as the substance itself becoming depleted such as by the binding or other desired interaction occurring.

Furthermore, the system may act to momentarily hold the substance (5) eliminated from the sample (1) such as in the location indicated for the collected fluidic substance (36). This can occur without disturbance such as might let the collected fluidic substance (36) remix as a result of it being eliminated from the sample (1) perhaps from turbulence or the like. This holding can simply be a pause in operation and thus the system may be considered as having a collected eliminated fluid pause element (31). This pause element may act at least some times after action of the substance transient elimination element. The holding of the eliminated substance can occur for a variety of times, such as times less than or equal to about 4 seconds, 3 seconds, 1.5 seconds, 1 seconds or even 500 ms. Through these times, the collected eliminated fluid pause element (31) may be configured to be a collected eliminated fluid pause element configures to hold for any of the above times. As indicated in FIG. 6, multiple pauses can be used and thus the system may have a multiple pause collected fluid pause element (33). This can occur repeatedly as well. In such a configuration, a sample processing system (2) can act to repeatedly momentarily hold a substance (5) eliminated from the sample (1).

As mentioned, movement of a fluid in the vicinity of the sample (1) may be desired for some embodiments. In this more general context, a sample processing system (2) according to one embodiment of the invention may be configured to include a sample interface microenvironment mix element (34). This sample interface microenvironment mix element (34) may actually be a substance mixer that acts after the substance source has dispensed its substance (5). This may act to mix of the substance during at least some part of a process. It may act to accomplish substantial mixing within the sample interface microenvironment (28). In such configurations, the system may act to accomplish substantial mixing within a particular area immediately adjacent to the sample (1). This area, termed the sample interface microenvironment or more generally a microenvironment (28) may be a variable thickness. For instance, in embodiments a sample interface microenvironment maybe next to the sample (1) to a depth of about of perhaps at least 20 μm from the sample (1). In some embodiments mixing may occur within smaller ranges as well. While at least a 20 μm microenvironment may be mixed in some embodiments, in other embodiments much smaller distances such as perhaps 10 μm, 1 μm, 500 nm, 200 nm, 100 nm, 50 nm and even within at least about 10 nm may be the area of interest. Mixing or replenishment in such a sample interface microenvironment (28) may be appropriate for a particular applications or configurations. Interestingly, as understood from the simple fact that existing systems do not afford such rapid processing, this microenvironment mixing does not occur in existing systems.

In mixing the substance (5) within the microenvironment (28), the sample processing system (2) can act with two different types of processes. An initial mixing may occur and then may be followed by a different type of mixing. In one embodiment, the system may act to initially more frequently and on a shorter time frame repeat a step of transiently substantially eliminating a substance from the sample (1). After these initial, perhaps more rapid steps, a second lower frequency or time period of repeating may occur. As one example, initially the sample processing system (2) may act with very little pause time in between the acts of eliminating and reapplying the substance (5). Following this initial action, the sample process system (2) may act more slowly to only occasionally eliminate material. Initial multiple steps may cause substantially more mixing and may permit the substance (5) to be replenished more quickly perhaps through number of initial repetitions of the step of transiently substantially eliminating the substance from a sample.

Referring to FIGS. 11 through 14, it can be understood how embodiment of the invention can serve to eliminate fluidic substance (10) from within the vicinity of sample (1). By including generally a substance transient elimination element (32), the sample processing system (2) may act to eliminate a substance (5) momentarily from within the immediate vicinity of the sample (1). Such a configuration may serve to transiently substantially eliminate an appropriate fluidic reactive substance from the sample (1). This may occur by substantially eliminating a fluid environment from within the immediate vicinity of the sample (1). In the embodiment shown, it can be seen that the system can act to decrease a bounded fluidic environment (15) and thus pullback the fluidic substance (10) from in the vicinity of the sample (1). This may occur through capillary action such as by the movement of a surface (7), perhaps a surface such as the microscopic slide (8). As shown, in one embodiment the microscopic slides (8) may be angularly moved apart and thus may act to decrease the restrictively confined fluidic environment (17). In this manner the movement mechanism and perhaps the programming may serve to act as a decreasing restrictive fluidic confinement element (35). This decreasing restrictive fluidic confinement element (35) may act to transiently substantially eliminate the substance from a sample (1). By transiently, that is in a manner consistent with an eventual reapplication, and substantially, that is such that a microenvironment is also largely removed so that it may be replenished, eliminating the substance (5) from the sample (1), the system can achieve goals for this embodiment. It may momentarily remove the substance (5) from the sample (1) in a manner such that the substance (5) may be reapplied to the sample (1) at some point in time. Furthermore, by substantially eliminating a substance (5) in the sample (1), the system may act to remove most of the substance (5) from in the vicinity of a sample (1). Naturally, some smaller amounts of substance (5) may remain, however, a significant portion of the substance (5) be removed and collected for appropriate mixing or reapplication. Thus, embodiments of the system may act to substantially eliminate the bounded fluidic environment from within the immediate vicinity of the exterior sample area (4) of the sample (1).

As can be seen in FIG. 4, collected fluidic substance (36) may be available within some proximity of the exterior sample area (4). This collected fluidic substance (36) may then be reapplied to the sample (1) perhaps through action of a substance reapplication element (37). This substance reapplication element (37) may act upon at least a portion of the transiently eliminated substance, perhaps most or all of that indicated as the collected fluidic substance (36). By reapplying at least a portion of the transiently substantially eliminated appropriate fluidic reactive substance, the sample processing system (2) act to replenish the microenvironment (28) caused by a fluidic substance (10) so that this microenvironment (28) is no longer depleted of the particular substance (5) of interest.

Similarly, a reapplication of the collected fluidic substance (36) may occur by increasing a bounded fluidic environment (15), that is, by increasing the restrictions on such an environment and thus making it smaller. By increasing the restrictively confined fluidic environment (17) the system may be considered as having an increasing restrictive fluidic confinement element (38). The increasing restrictive fluidic confinement element (38) can reapply at least a portion of a transiently substantially eliminated substance to a sample (1) such as the collected fluidic substance (36).

In some embodiments, capillary action can be used to move the fluid as desired. By decreasing a restrictively confined fluidic environment (17) in the presence of particular substances and surface materials, the fluidic substance (10) may be pulled back by capillary action. In embodiments, this can even occur at a speed that is greater than a capillary movement speed for a particular configuration. If the surfaces (7) such as the microscopic slides (8) are angularly pulled apart at a speed that causes the fluidic substance (10) to move more rapidly than it would move normally through capillary action without movement, the system may be considered as presenting a greater than a capillary movement speed fluid movement element (39). Furthermore, the sample processing system (2) can be configured to provide a capillary displacement element (40) and perhaps one that serves as a capillary fluid displacement element. In addition, the capillary displacement element (40) can serve as a capillary action substance application element (41) by moving a fluid back on to a sample (1). Capillary action may exist with a capillary capable liquid, that is a liquid that exhibit capillary action for a particular configuration or the like. Such a liquid may also include a liquid exhibiting surface tension or a surface tension liquid.

Other types of movement are also possible, for instance, it is possible to have a hydraulically displaced fluid in the vicinity of at least a portion of an exterior sample area (4). A system may include a hydraulic displacement element or the like. In general, if using a capillary action, a system can be considered as having a capillary fluid displacement element for displacing a fluid in the vicinity of at least a portion of the exterior sample area (4). It may also be considered as acting to capillarly eliminate a fluid environment when it pulls a fluidic substance (10) away from the sample (1).

Accomplishing movement at a speed greater than a capillary movement speed for a particular configuration, the system can be considered as presenting a fast fluid movement. This, of course, can include fast fluid application as well as fast fluid elimination. This may exist in any situation in which fluid movement occurs faster than a normal capillary movement for a particular configuration, and thus the system can be considered as presenting a fast fluid movement element. Fast fluid movement can occur across the sample at speeds which may range from at least equal to about 0.05 m/s, 0.1 m/s, 0.125 m/s, 0.25 m/s, 0.5 m/s, and perhaps as great as at least about 1 m/s. Thus a fluid movement element (42) may be configured to accomplish any of the mentioned fluid movement speeds or other speeds as appropriate. In embodiments, a fluid movement element (42) can accomplish a fluid movement in an amount of time rather than a particular speed. For configurations as shown where the sample (1) is situated on a microscopic slide (8), an amount of time could be a time such as less than or equal to about one second, one half second, 400 ms, 200 ms, 100 ms, or even 50 ms.

By referring to FIGS. 11 through 14, it can be understood that a variety of mechanical arrangements can be used to achieve the mentioned rapid sample processing. In one type of mechanical embodiment, multiple samples (1) can be configured in an aligned arrangement. FIG. 11 shows that an upper glass microscope slide (43) can be connected to an upper slide holder (44). Similarly, a lower glass microscope slide (45) can be held by a lower slide holder (46). Both the upper slide holder (44) and the lower slide holder (46) can be connected through some type of hinged movement element (47). The hinged movement element (47) may act to permit some sort of angular movement between slide holders and thus the upper glass microscope slide (43) and the lower glass microscope slide (45). In a general sense, the hinged movement element (47) may simply cause some angular movement component between a first and a second surface, such as the microscope slides (8) or other types of surfaces. This movement can occur through use of a motor, perhaps a stepper motor under computer control such as lower slide holder motor (48) and upper slide holder motor (49).

A hinged movement element (47) may serve as a first and second surface movement element. While the surfaces shown in the figures are actually microscopic slides, it should be understood that the surfaces need not be planar. They may be substantially planar or flat; they can be curved as well. In FIGS. 4 and 14, when the hinged movement element (47) is in a closed position, the upper glass microscope slide (43) may be in close proximity to the lower glass microscope slide (45). Through some operation whether it be through software, hardware, or perhaps firmware, the sample processing system (2) may be considered to include a close proximity surface displacement element. This close proximity surface displacement element can serve to permit movement or displacement of one surface relative to another while also permitting positioning at some point where the surfaces are in close proximity to one another. In one embodiment, the invention can be configured to displace the first surface relative to and in close proximity to the second surface. The surfaces of course may be, but need not be, microscopic slides (8).

As mentioned earlier, a motive force element (23) can cause angular or other movement between a first surface relative to its second surface. Angular movement can be seen by comparing the movements shown in FIGS. 4, and 11 through 14. It can be seen that the sample processing system (2) may be considered to include first and second surface angular movement element. This element can act to displace a first surface relative to and in close proximity to a second surface. While different aspects of these movements are shown in FIGS. 4, and 11 through 14, it should be understood that the ultimate sequencing achieved by an automatically sequenced test processor (3) can include many variations of these movements. As shown in FIG. 6 a specialized sequence of movements can be achieved to accomplish a particular application that subjects the sample to a substance, transiently eliminates that substance, mixes the substance, reapplies the substance, and ultimately withdraws the substance from a sample (1). As indicated, various step timings and sequences can be achieved. For example as shown in step three and four, an initial sequence of ways to mix a primary antibody can be achieved followed by a wave sequence that may permit significant incubation time periods in general. It can also be noticed through FIG. 6 that an entire detection sequence can be achieved in less than 15 minutes—a significantly reduced time period as compared to most existing systems.

As shown in FIG. 4 it can be seen how the angular movement element can actually achieve elimination and reapplication of a fluidic substance (10). Viewing the sequence shown in FIG. 4 in the order A-B-C as but one example of a sequence, it can be seen how closing the slides together can cause the sample (1) to be subjected to a fluidic substance (10). FIG. 4 shows how the two surfaces, in this case microscopic slides (8) can be in an open position. In this arrangement, the fluidic substance (10) is eliminated from in the vicinity of, and is eliminated from, an exterior sample area (4) of the sample (1). As shown, this may occur through capillary action whereby the fluidic substance (10) is pulled back from the sample (1) perhaps by the natural tendency of the fluid in such an arrangement.

FIG. 4 shows the microscopic slides (8) in an intermediate position. As can be understood, the fluidic substance (10) may be pulled along the area in between a microscopic slide (8) and may pass across the exterior sample area (4). FIG. 4 shows how in one embodiment the microscopic slides (8) may be moved to a closed position and are in close proximity to each other. First, it can be understood that the fluidic substance (10) may now be fully covering all appropriate areas between the microscopic slides (8). Furthermore, in the figure it can be seen that the microscopic slides may not actually be perfectly parallel to each other when they are in the closed position. The microscopic slides (8) may have attached to themselves some type of identifier. This identifier, shown in FIG. 4 as labels (50) can cause spacing through their own thickness. In instances where the identifiers or perhaps labels (50) are relatively thick, it is possible that the microscopic slides (8) do not become fully parallel and the spacing may even be narrower at the other end. This is shown in FIG. 4 as one possibility. Minimizing spacing can serve not only to reduce fluid but also to permit the use of existing label arrangements—even if not optimum.

The reverse sequence should also be understood. Considering FIG. 4 in the order C-B-A, it can be understood how the fluid movement element (42) can act to not only apply fluid to the sample (1) (as in the A-B-C case) but also to eliminate the fluid from a sample (1) (as in the C-B-A case). Again, with FIG. 4 depicting two surfaces in close proximity to each other, when the surfaces are moved apart in an angular fashion, they may ask to eliminate fluid from the exterior sample area (4) of the sample (1). As shown in FIG. 4 as the surfaces or perhaps the microscopic slides (8) are moved apart, the fluidic substance (10) may start moving back toward the hinged movement element (47). As the two surfaces continue to increase their angular movement, a full elimination of fluid can occur. Ultimately it may be sufficient that the fluidic substance (10) is moved beyond the exterior surface area (4) of the sample (1) and is ultimately collected in some other location. Thus, as can be understood from FIG. 4 how to collected fluidic substance (36) may exist as a result of the motive force element (23) acting upon the fluidic substance (10). Once eliminated from an exterior sample area (4), the collected fluidic substance (36) can become mixed to some degree and can be ready for reapplication.

Naturally a variety of spacings are also possible. In the embodiment shown in FIG. 4, in the close proximity position, the surfaces may be substantially parallel even though not perfectly parallel. The distances between the two surfaces can vary based on the particular needs of the substance (5) or perhaps the sample (1). In instances in which the sample processing system (2) is configured for immunohistochemical processing, it may be appropriate to use close proximity surfaces that are separated by 100, 200, 250, and perhaps as little as at most about 300 μm. Furthermore the separation (perhaps of at least one end) can be established by the identifier or perhaps label (50) thicknesses. As shown in FIG. 4, one end of the surfaces may be approximately two label thicknesses apart. Similarly in situations where one of the microscopic slides (8) either does not contain a sample or has no label on it, the microscopic slide (8) may be separated on one end by only one label or identifier thickness.

Referring to FIGS. 8, and 16-18, it can be seen that a plurality of samples (1) may be held by a plurality of sample holders. In such an arrangement, it can be seen that the microscopic slides (8) may be held in place by some sort of slide retention element, perhaps such as a slide retention spring (51). Of course, other arrangement are possible. In such an arrangement, multiple samples can be processed coincidentally. For convenience, these multiple samples may be placed adjacent to each other and moved as one. In this configuration, the sample processing system (2) may have a sample holder that serves as a multiple, close proximity, substantially parallel or perhaps planar holder for a particular type of sample, a microscopic slide, or perhaps merely surfaces.

The sample holder may also serve as a multiple, close proximity, substantially parallelly-oriented sample surface pair or perhaps even a proximally paired sample or surface as shown in FIGS. 10 through 18. As mentioned with reference to FIG. 4, it is possible to vary the spacing in order to alter the amount of fluid involved. As shown in FIGS. 3 and 4, this microenvironment (28) may be within a volume immediately adjacent a sample (1). By capillary or other action causing the elimination or at least substantial elimination of the fluidic substance (10) (some fluidic substance may remain on a sample) the system can act to cause an adequate or even total removal of the microenvironment (28). By eliminating the fluidic substance (10) and pulling it back into a collected fluid substance fluidic substance (36) the fluidic substance (10) may be refreshed and mixed.

A variety of fluid volumes may be used of course. In an embodiment and configuration where the system is designed for use to accomplish immunohistochemistry with a microscopic slide, it may be appropriate to move less than or equal to about 300, 225, or even 200 µl of a fluid. This movement may occur in at least a portion of the restrictively confined fluidic environment and they occur by eliminating the microenvironment (28). Thus, the sample processing system (2) may be considered as having elements configured to move less than or equal to about any of the amounts of fluid mentioned earlier. Through consideration of particular substances and a range of samples, it may be appropriate to move a minimal amount of a substance (5) or perhaps fluidic substance (10). This minimal amount may be an amount that permits adequate replenishment of a microenvironment (28), or that permits adequate interaction between this sample (1) and the substance (5) in a selected process time period. In situations where there are different or lesser demands on the time for processing it may be possible to even further reduce a volume of fluidic substance (10) and still permit adequate interaction between the sample (1) and the substance (5) in a desired time frame. As such the system may be configured to use a lesser amount of substance, rather than to minimize time.

FIG. 6 is a table that shows that a variety of repetitious actions that can be accomplished in one example of a sequence. As shown, the automatically sequenced test processor (3) can repeatedly mix or otherwise act upon a substance (5) or perhaps a sample (1). Referring to step three, it can be noticed that a sequence may be used to initially mix a primary antibody. Such mixing may involve, as but one example, three sequences where the fluidic substance (10) is pooled as a collected fluidic substance (36) and eliminated from the exterior sample area (4). This may be held for a relative short time period (or no time period at all) such as approximately 1.5 seconds. Similarly, during the initial mix action the fluidic substance (10) may be held exposed to and reapplied to the sample (1) for some time (or again, or no time period at all) such as in one example, two seconds.

Referring to step 4 in the exemplary sequence shown in FIG. 6, the values indicate that immediately following this initial fast wave action there may be a slower wave action with exposed incubation lasting perhaps as long as 22 seconds. This may be repeated, perhaps as shown for six times or the like. While this represents but one particular test sequence, in general it should be understood that repeated actions can occur. By its programming the sample processing system (2) or perhaps also the automatically sequenced test processor (3) may be considered as including not only a repetitious action element but also perhaps in this instance a repetitious action fluid wave element. Through steps such as the steps three and four as shown in FIG. 6, the system can act to repeatedly transiently substantially eliminating the substance from the sample (1). Naturally other repetitious action elements are possible, and these may include repetitious action elements such as: a repetitious action fluid wave element, as mentioned above, a repetitious action substance elimination element, a repetitious action substance reapplication element, a repetitious action incubation element, or the like. In instances where at least two repetitious actions are contemplated, the system may be considered as having an at least two action repetitious action element, etc. The repetitious actions may occur regularly or perhaps irregularly. In the example shown in FIG. 6, this particular sequence of steps three and four involves two different regular time intervals for at least a portion of the overall process. Thus, step three involves three repeats with a regular time interval and step four involves six repeats with a regular time interval. In some embodiment the automatically sequenced test processor (3) may repeatedly reapply at least a portion of a transiently substantially eliminated substance.

The repeating activity may occur more than one, two, three, four or perhaps even five times. As shown in FIG. 6, it may occur three times for an initial mixing, six times for a primary antibody incubation and perhaps four times for an initial chromogen or perhaps two-step substance mixing. Similarly, for a counterstain it may occur four times with an incubation or dwell time of perhaps four seconds as shown. In some embodiments particularly those configured for immunohistochemistry, 3, 6 and 9 repetitions may be appropriate for first antibody substances, chromogens, or counterstain substances. Through this action, it can be understood how the system can act to repeatedly and non-replacingly substantially refresh the substance in a microenvironment (28). This microenvironment may be situated adjacent to the sample to permit shorter partial interaction time as well as a shorter overall processing time in order to permit more rapid processing. Through this action the system can be considered as repeatedly causing a fluid wave within a bounded fluidic environment (15). This can occur with a variety of frequencies including but not limited to the range of times present in the ones specific test sequence shown in FIG. 6 as well as other frequencies. As may be understood from the variations shown for the specific substance and sequences indicated in FIG. 6, the mixing can occur with differing occurrences for differing substances. This is also true of the elimination and reapplication steps. Furthermore the amount of time a collected fluidic substance (36) is held eliminated from the exterior sample area (4) vary as well.

As mentioned, the system may act to automatically withdrawal a substance such as a fluidic substance from within proximity to sample. This can occur by using an absorbent material (72). This absorbent material may be a wicking material. A substance withdrawal element (53) may be configured to withdraw substance from one or more samples. It may act to come transient contact at a location where fluidic substance exists. This transient contact location. may be selected as a particularly desirable location from which to withdraw a fluidic substance. As mentioned the withdrawal of the spent substance may be through a wicking element (73). The wicking element (73) can act to pick away a substance from it proximity of the sample. This wicking can exist by or because of capillary action and thus the wicking element may present a capillary action substance withdrawal element. Withdrawal of this substance from a sample can be enhanced in some fashions. In embodiments, the system may be configured to provide an enhanced withdrawal orientation element. This element may be an enhanced withdrawal orientation sample tilt element (74). By establishing a substance withdrawal enhancement condition for the sample (1), the system may facilitate withdrawal while the substance withdrawal enhancement condition is established. This substance withdrawal enhancement element (74) can be both programming and mechanical operation. In one embodiment, the system may act to tilt sample to an enhanced withdrawal orientation. This may involve orienting a surface to facilitate wicking of a substance, establishing a tilted surface, establishing an untilted surface, and establishing surfaces at least about 22.5°, 30°, 45°, and perhaps 67.5°. Furthermore when surfaces are angled with respect to each other a bisected angle between the two surfaces, may be tilted. Again, this can occur at various angles perhaps at least about 22.5°, 45°, and 90°.

FIGS. 15, 25, and 26 depict a perpendicular absorbent wicking roll (52); FIGS. 7 and 8, and to some extent 27-30 depict systems configured with a parallel substance withdrawal element (53) and having upper and lower slide cameras (63 and 64). When any particular fluidic substance (10) has accomplished its function and is no longer needed, that substance (5) may be withdrawn. This withdrawal can occur in a variety of fashions perhaps such as by automatically moving an absorbent material to a position in the vicinity of the sample. Thus, system may have absorbent material movement element (75). In the embodiments of the system, the absorbent material movement element (75) may be a linear absorbent material movement element that may permit an absorbent material to move along a straight path forward and backward when needed. When extended, the absorbent material may make contact with at least some of the fluidic substance. In embodiments where the absorbent material is contained within it confinement enclosure, the system may act to automatically move the confinement enclosure and achieve the withdrawal of substance. When extended, it absorbent material may even be pressed past a point of initial contact to assure adequate wicking. Thus, the system may contain an absorbent material substance pressure element (76) such as may be contained in programming of or hardware constituting a movement mechanism.

As mentioned earlier, the absorbent material may be encased in confinement enclosure (75). This confinement closure (75) may be configured to substantially encase the absorbent material. Furthermore, in instances where multiple samples and perhaps varying amounts of multiple samples the system may be configured to establish a coordinated exposed area of absorbent material that is appropriate for an anticipated amount of a substance to be withdrawn. By coordinating an absorbent material parameter, be it width, length, type of with material, thickness, or the like, the system can be assured of not reaching a saturation level—especially when adjacent samples are involved. Thus, the absorbent material may have a multiple sample saturation coordinated parameter. The absorbent material exposed area may be coordinated for an anticipated amount of substance.

As mentioned, the substance withdrawal element may be enclosed and may present a cassette. This cassette or other enclosure may be removably engaged by some removable engagement element, perhaps a snap arrangement. The operation may be accomplished by merely extending and then retracting the wicking cassette or other substance withdrawal element. The substance be removed from any further interaction, and it may be appropriate to withdraw the substance by some type of wick element. This wick element may also act to capillarly withdraw the substance from proximity to the sample (1) upon the completion of at least a portion of the process. As shown in FIG. 6, in one representative test sequence, the withdrawal of the fluidic substance (10) can occur multiple times throughout the overall process. For instance, steps 5, 8, 11, 15, 18, 21, etc., indicate that at multiple times a particular substance is withdrawn from the sample (1) as part of the overall test sequence. Withdrawal can also occur at times when no substance is supposed to be on a sample such as that shown in step 1. At this point in time this could be considered unnecessary however it may serve to assure that the sample(s) are dry and ready to begin processing. As understood from FIGS. 7, 8, and 27-30, this cassette may be arranged with a parallel major axis that is oriented with a plurality of samples and thus the system may have a parallel major axis orientation element (76). As shown in FIGS. 15, 25, and 26, it may also be oriented in a perpendicular fashion, perhaps with a perpendicular major axis orientation element (77). While FIGS. 15, 25, and 26 show a perpendicular orientation element, FIGS. 7 and 8, and 27 through 30 indicate a parallel embodiment in which one cassette can be used. As shown, the upper and lower slide holders (49 and 48) may be arranged so that microscopic slides (8) are configured in a row of pairs along a pivot axis of a hinged movement element (47). This holder is one type of linearly arranged plural sample holder. As such, when fluidic substance (10) is transiently eliminated it becomes a collected fluidic substance (36) closest to the pivot axis of the hinged movement element (47). Furthermore to facilitate withdrawal of the substance the upper and lower slide holders (49 and 48) may be tiled. At this point, a parallel wicking cassette can be moved into place to coincidentally withdraw the spent substance from within the vicinity of the samples (1). As shown the substance withdrawal element (53) can be established so that the absorbent material is configured in a median angular orientation relative to the samples. In this arrangement, the major axis of the absorbent material, that is the axis of the long dimension of its exposed material is parallel to a plurality of linearly arranged samples. Furthermore, the cassette itself may be tilted to correspond to any tilt of the samples, perhaps by being aligned with a bisected angle. Thus the mechanical configuration (in this embodiment) may serve as a median angular orientation element which orients the absorbent material appropriately for withdrawal of the collected fluidic substance (36).

Regardless of whether the absorbent material (72) is used in a cassette or other arrangement, embodiments may include multiple amounts of absorbent material (72) that may be sequenced so that in the series of actions in any test or in separate tests, multiple events of withdrawing differing spent substances can occur. Thus, additional amounts of unused portions of a larger amount of absorbent material (72) may be presented to a location such as that of a collected fluidic substance (36) or merely in the vicinity of the sample (1) or the samples (1). To accomplish this, embodiments can include an absorbent material sequence element (78). Through action of the automatically sequenced test processor (3), or more generally, the sample processing system (2), the system may act to automatically sequence the absorbent material so that an unused portion is sequentially presented at appropriate times. This may occur through an absorbent material advance element that establishes an unused portion of absorbent material in an exposed position as part of the biochemical or other test sequence. In addition, embodiments may advance or sequence the material in appropriate amounts perhaps incrementally and so there may be included, perhaps through programming or the like, an absorbent material multiple sample appropriate incremental advance element that acts to only sequence an appropriate amount based on how many samples were processed.

As shown in FIGS. 27 through 30, in one embodiment, a more common cassette arrangement such as that with a rotation element, perhaps multiple roller elements, can be used. Whether in an absorbent material roller system or otherwise, embodiments may act to accumulate a used portion separate from an unused portion. This may occur through a used absorbent material accumulator that may even rotate an element and roll some of the absorbent material. Two rollers may be used so that one acts to unroll an unused portion of absorbent material perhaps through an unused portion roller (79), while another acts to roll-up a used portion of absorbent material, perhaps through a used portion roller (80). These may be coordinated so that the unused portion roller acts when the used portion roller does. A two reel absorbent material roller cassette can be used perhaps so that the system can be considered as continuously rolling two reels of absorbent material, that is sequencing through material at appropriate times and perhaps even in appropriate increments until the entire cassette has been used.

As mentioned, the absorbent material can be advanced in multiple sample appropriate increments. In embodiments such as shown in FIGS. 10 and 16 through 18 that have upper and lower slide holders (49 and 48) arranged in a row as one type of linearly arranged plural sample holder, the sample processing system (2) may be operated in a manner in which not all positions are used in all test runs. In such a manner, or otherwise, it may be appropriate to use an altered amount of absorbent material (72). For example, while a row of eight sample pairs is presented in the embodiment shown in FIGS. 10 and 16 through 18, perhaps only five samples may need to be run with three different tests. In such an instance, three locations (two pairs and one run by itself) may be actioned. If perhaps ten withdrawal events are needed for each of these tests (e.g., primary antibody, rinse, secondary antibody, rinse, chromogen 1, rinse, chromogen 2, rinse, counterstain, rinse) only 30 singular withdrawal spots may be needed. Rather than using withdrawal programming for when a full sample holder is used, where 80 singular withdrawal spots may have been needed, the system may automatically act to advance in multiple sample appropriate increments and thus conserve absorbent material (72). Furthermore, since a cassette or the like may have only a finite amount of total absorbent material, the system can track the multiple sample appropriate increments and perhaps totalize them through programming or the like that may act as a multiple sample appropriate increment tracker element. It may even inform an operator when it may be appropriate to replace an element such as a cassette or the like.

In presenting an exposed, likely unused portion of the absorbent material (72), embodiments may act to tension an unused portion of the absorbent material in an exposed position. Thus can occur through an absorbent material tension element perhaps such as through exposed material rollers (81) or the like between which said unused portion is tensioned as it is exposed to the spent fluidic substance. Two material rollers may be used as shown, and these may also help to reduce any wicking into the unused material roll during nonuse, so that the next run still present fresh, fully absorbent material.

FIGS. 11 through 14 and 16, show that chemical interaction may occur where the surfaces are, or at least one surface is, in an untilted orientation. By establishing an untilted surface, it may be easier to facilitate reagent dispensing on a surface such as a microscopic slide (8) such as by extending and retracting a reagent container (55) relative to a desired position or the like. The substance (5) may then be dispensed perhaps drop-wise or in an appropriate metered amount. At times when it is desirable to withdraw a particular fluidic substance (10) from an exterior sample area (4) from proximity to the sample (1), it may be desirable to facilitate this withdrawal of the substance in some manner. This can be facilitated in a variety of ways. In one embodiment this may include orienting a surface to facilitate the withdrawal of the substance away from proximity to the sample. As shown in FIG. 15, this orientation may involve establishing a tilted surface or perhaps tilting the surface to facilitate the wicking away of the substance. This orientation, or perhaps tilting, can occur at a variety of angles and can establish either an upper or lower surface at a given angle or perhaps a bisected angle at a given angle relative to horizontal. This bisected angle may actually be a line in between the two surfaces and may be oriented at a particular angle. As shown in FIG. 15 in one embodiment the orientation may be the tilting of a bisected angle (54) at an angle such as 45°. In this configuration, the surface, perhaps a lower glass microscope slide (45), may be established at perhaps greater than 30° or even 22½°. Similarly the upper surface such as the upper glass microscope slide (43) may be established at a different angle perhaps 60° or 67.5°. In this fashion it can be understood that the withdrawal of the fluidic substance by something such as the perpendicular wicking roll (52) as shown in FIGS. 15, 25, and 26 or perhaps the more general substance withdrawal element (53) such as perhaps a wicking cassette or the like may be moved into position to withdraw a liquid that has collected closer to the hinged movement element (47). Of course, 90° could be used for any surface or perhaps even for the bisected angle (54). In some configurations it may be appropriate to establish a tilted bisected angle (54) between the two surfaces while accomplishing the step of wicking or more generally withdrawing a substance (5) from proximity to the sample (1). This may also occur with one surface untilted such as might be desired to eliminate some movement element or motor or the like.

An aspect of some embodiments may be the fact that the sample process system (2) may act substantially coincidentally on all samples contained. From FIGS. 10, 16, 17, 18, and 19 it may be understood that one appropriate configuration of the system may present a substantially coincident sample treatment element to which multiple samples are responsive. In the configuration shown this may involve the multiple sample holders shown. Such a system may also involve the use of individual or location specific reagent containers (55). These may dispense from a side actuator button (61) as shown in FIG. 19, from a top actuator (62) as shown in FIGS. 20-24, or otherwise. As shown in FIG. 12, the reagent containers (55) can move or otherwise place reagent on each microscopic slide pair. Further, as may be understood from FIGS. 20-24, the reagent containers (55) may be configured to include one or more of a cartridge (65) or a magazine (66). The cartridge (65) may be a container for a single antibody substance or the like, perhaps such as the primary antibody substance. The magazine may be a single container for multiple substances with multiple chambers and thus may present a single container multiple chamber multiple fluidic substance magazine (69). It may also be configured in somewhat of a line and thus present a linear reagent magazine such as is shown in one embodiment. The system may include a single container multiple chamber multiple fluidic substance magazine whereby a single container may have multiple chambers with in it so that multiple fluidic substances can be placed in the chambers. In one arrangement, a dispensement force element (68) may be used to release substance from the single container multiple chamber multiple fluidic substance magazine (69). By having at least two substance chambers, the system can act automatically to determine which substance or interactive fluidic substance is appropriate and can then dispense that substance. All that may be necessary for the operator is the place the single container multiple chamber multiple fluidic substance magazine (69) in the system. In order to facilitate processing that differs by location, the system may be configured to include location specific sources. These location specific sources may even have a correspondence with sample of locations. By including multiple substance source magazines, as one type of a location specific multiple substance source, differing substances can be dispensed on one sample throughout the course of an automated test sequence. In addition, the system may include location specific single substance sources as well. Thus the system may include a single container multiple chamber multiple fluidic substance magazine (69), a linearly disposed multiple substance source (70), or even a primary antibody cartridge (71) as shown in FIGS. 20 through 24. Thus, the system can act to automatically process samples even when differing substances are required.

In order to minimize operator requirements when multiple runs may occur, the multiple substance source may include functionally related substances. furthermore substances can have volumes relative to their predicted usages. in this manner consistent may include a functionally related multiple substance source magazine, and even a relative substance use sized source. To facilitate dispensement of the substance onto the sample, the multiple source may be arranged in a row and moved as appropriate to permit the selected substance to be dispensed. as shown in FIGS. 20 through 24, the multiple substance source a being linearly disposed multiple substance source (70). Since primary antibody substances are of particular value, a separate single substance source, perhaps a primary antibody cartridge (71) can be used. This can be a separate item or, and shown in FIGS. 20 through 24, it may even snap into the multiple substance source magazine.

Appropriate mechanisms and software can achieve sampling and other processing on all samples coincidentally. Thus the samples may be treated virtually identically in terms of the process sequences while yet having their own particular substance selections as may be appropriate. This may involve not only coincidentally acting all in all samples but also substantially evenly subjecting all samples to an appropriate fluidic reactive substance such as at the same time or the like. All actions may even occur coincidentally in some embodiments. The system though its programming may be considered as including a substantially coincident sample treatment element. This substantially coincident sample treatment element may also act substantially evenly with respect to its movement actions.

As may be understood with reference to FIG. 9, it can be seen that different primary antibody substances and even different to other substances may be included for individual slide locations. Thus, different substances may be dispensed while yet permitting all samples to be treated substantially evenly and perhaps coincidentally. As mentioned earlier, reagents may snap into specific locations. An operator a snap in at least one source, or they may even snap in or somehow otherwise detachably connect even a linear multiple reagent magazine. Thus, the system can be considered as having a snap securable location specific substance source, a snap securable primary antibody substance cartridge, or even a snap securable linear multiple reagent magazine.

As can be easily understood from the foregoing, the basic concepts of the present invention may be embodied in a variety of ways. It involves both processing techniques as well as devices to accomplish the appropriate processing. In this application, the processing techniques are disclosed as part of the results shown to be achieved by the various devices described, as described steps, and as steps that are inherent to utilization as are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims and method or process claims are support regardless of the nature of the discussion.

A variety of changes may be made without departing from the essence of the invention. Such changes are also implicitly included in the description. They still fall within the scope of this invention. A broad disclosure encompassing both the explicit embodiments shown, the great variety of implicit alternative embodiments, and the broad methods or processes and the like are encompassed by this disclosure. It also should be understood that language changes and broader or more detailed claiming may be accomplished at a later date. With this understanding, the reader should be aware that this disclosure is to be understood to support as broad or narrow a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "dispenser" should be understood to encompass disclosure of the act of "dispensing"—whether explicitly discussed or not—and, conversely, were there effectively disclosure of the act of "dispensing", such a disclosure should be understood to encompass disclosure of a "dispenser" and even a "means for dispensing." Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in following list of references or other documents or references filed with the application are hereby appended and hereby incorporated by reference, however, as to each of these, to the extent that such information or statements incorporated by reference might be considered inconsistent with the patenting of this/these invention(s) such statements are expressly not to be considered as made by the applicant(s):

I. U.S. Patent Documents

| DOCUMENT NO. & & KIND CODE (if known) | PUB'N DATE mm-dd-yyyy | PATENTEE OR APPLICANT NAME | Pages, Columns, Lines Where Relevant Passages Or Relevant Drawings Appear |
|---|---|---|---|
| 2,039,219 | Apr. 28, 1936 | Hausser, et al. | |
| 2002/0142470 A1 | Oct. 3, 2002 | Clarke et al. | |
| 2002/0182623 A1 | Dec. 5, 2002 | Lefevre et al. | |
| 2003/0124729 A1 | Jul. 3, 2003 | Christensen et al. | |
| 2003/0138877 A1 | Jul. 24, 2003 | Gibbs et al. | |
| 2003/0203493 A1 | Oct. 30, 2003 | Lemme et al. | |
| 2004/0033163 A1 | Feb. 19, 2004 | Tseung et al. | |
| 2004/0043495 A1 | Mar. 2, 2004 | Stokes et al. | |
| 2004/0191128 A1 | Sep. 30, 2004 | Bogen et al. | |
| 2004/0241050 A1 | Dec. 2, 2004 | Bogen et al. | |
| 3,777,283 | Dec. 4. 1973 | Elkins | |
| 4,034,700 | Jul. 12, 1977 | Bassett et al. | |
| 4,043,292 | Aug. 23, 1977 | Rogers et al. | |
| 4,199,613 | Apr. 22, 1980 | Johnson | |
| 4,378,333 | Mar. 29, 1983 | Laipply | |
| 4,501,496 | Feb. 26, 1985 | Griffin | |
| 4,505,557 | Mar. 19, 1985 | Golias | |
| 4,731,335 | Mar. 15, 1988 | Brigati | |
| 4,777,020 | Oct. 11, 1988 | Brigati | |
| 4,790,640 | Dec. 13, 1988 | Nason | |
| 4,801,431 | Jan. 31, 1989 | Cuomo et al. | |
| 4,847,208 | Jul. 11, 1989 | Bogen | |
| 4,985,206 | Jan. 15, 1991 | Bowman et al. | |
| 5,023,187 | Jun. 11, 1991 | Koebler et al. | |
| 5,068,091 | Nov. 26, 1991 | Toya | |
| 5,338,358 | Aug. 16, 1994 | Mizusawa et al. | |
| 5,425,918 | Jun. 20, 1995 | Healey et al. | |
| 5,569,607 | Oct. 29, 1996 | Simon et al. | |
| 5,650,327 | Jul. 22, 1977 | Copeland et al. | |
| 5,654,199 | Aug. 5, 1997 | Copeland et al. | |
| 5,654,200 | Aug. 5, 1997 | Copeland et al. | |
| 5,804,141 | Sep. 8, 1998 | Chianese | |
| 5,839,091 | Nov. 17, 1998 | Rhett et al. | |
| 5,948,358 | Sep. 7, 1999 | Kalra et al. | |
| 6,096,271 | Aug. 1, 2000 | Bogen et al. | |
| 6,165,739 | Dec. 26. 2000 | Clatch | |
| 6,183,693 B1 | Feb. 6, 2001 | Bogen et al. | |
| 6,218,191 B1 | Apr. 17, 2001 | Palander | |
| 6,296,809 B1 | Oct. 2, 2001 | Richards et al. | |
| 6,349,264 B1 | Feb. 19, 2002 | Rhett et al. | |
| 6,352,861 B1 | Mar. 5, 2002 | Copeland et al. | |
| 6,495,106 B1 | Dec. 17, 2002 | Kalra et al. | |
| 6,541,261 B1 | Apr. 1, 2003 | Bogen et al. | |
| 6,544,798 B1 | Apr, 8, 2003 | Christensen et al. | |
| 6,582,962 B1 | Jun. 24, 2003 | Richards et al. | |
| 6,703,247 B1 | Mar. 9, 2004 | Chu | |
| 6,735,531 B2 | May 11, 2004 | Rhett et al. | |
| 6,735,531 B2 | May 11, 2004 | Rhett et al. | |
| 6,746,851 B1 | Jun. 8, 2004 | Tseung et al. | |
| 6,783,733 B2 | Aug. 31, 2004 | Bogen et al. | |
| 6,827,901 B2 | Dec. 7, 2004 | Copeland et al. | |

II. Other Documents

U.S. Provisional Application No. 60/673,468, filed Apr. 21, 2005, Entitled Method and Apparatus for Automated Rapid Immunohistochemistry Thus, the applicant should be understood to have support to claim and make a statement of invention to at least: i) each of the processing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented. In addition and as to computer aspects and each aspect amenable to programming or other electronic automation, the applicant should be understood to have support to claim and make a statement of invention to at least: xiii) processes performed with the aid of or on a computer as described throughout the above discussion, xiv) a programmable apparatus as described throughout the above discussion, xv) a computer readable memory encoded with data to direct a computer comprising means or elements which function as described throughout the above discussion, xvi) a computer configured as herein disclosed and described, xvii) individual or combined subroutines and programs as herein disclosed and described, xviii) the related methods disclosed and described, xix) similar, equivalent, and even implicit variations of each of these systems and methods, xx) those alternative designs which accomplish each of the functions shown as are disclosed and described, xxi) those alternative designs and methods which accomplish each of the functions shown as are implicit to accomplish that which is disclosed and described, xxii) each feature, component, and step shown as separate and independent inventions, and xxiii) the various combinations and permutations of each of the above.

With regard to claims now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The invention claimed is:

1. A method of sample processing comprising the steps of:
    a. obtaining a sample;
    b. establishing said sample on a sample holder;
    c. selecting a biochemical test sequence for said sample;
    d. subjecting at least a portion of an exterior sample area of said sample on said sample holder to at least one fluidic substance;
    e. automatically sequencing an absorbent material to establish an unused portion of absorbent material in an exposed position as part of said biochemical test sequence;
    f. extending said unused portion of said absorbent material in said exposed position to said fluidic substance on said sample holder;
    g. contacting said unused portion of absorbent material and said fluidic substance on said sample holder;
    h. automatically withdrawing said fluidic substance to said unused portion of said absorbent material as part of said biochemical test sequence;
    i. retracting said absorbent material from said sample holder; and
    j. accomplishing desired results for said biochemical test sequence.

2. A method of sample processing as described in claim 1 wherein said step of automatically withdrawing said fluidic substance as part of said biochemical test sequence comprises a step selected from a group consisting of capillarly withdrawing said substance from proximity to said sample upon completion of at least a portion of a process and wicking said substance away from proximity to said sample upon completion of at least a portion of a process.

3. A method of sample processing as described in claim 2 wherein said step of capillarly withdrawing said substance from proximity to said sample upon completion of at least a portion of a process comprises the step of wicking said substance away from proximity to said sample upon completion of at least a portion of a process.

4. A method of sample processing as described in claim 3 wherein said processing comprises a step selected from a group consisting of:
   accomplishing an immunohistochemistry process,
   accomplishing an immunocytochemistry process,
   accomplishing an in situ hybridization process,
   accomplishing a fluorescent in situ hybridization process,
   accomplishing a chromosomal identification process,
   accomplishing a staining process,
   accomplishing an antigen retrieval process,
   accomplishing a cytochemical process,
   accomplishing a histochemical process,
   accomplishing a molecular chemical process,
   accomplishing an epitope retrieval process, and
   accomplishing a pretreatment process.

5. A method of sample processing as described in claim 1 wherein said step of automatically sequencing an absorbent material to establish an unused portion of absorbent material in an exposed position as part of said biochemical test sequence comprises the steps of:
   rotating an element;
   rolling an unused portion of said absorbent material; and
   rolling a used portion of said absorbent material in coordination with said step of rolling an unused portion of said absorbent material.

6. A method of sample processing as described in claim 5 wherein said step of automatically sequencing an absorbent material to establish an unused portion of absorbent material in an exposed position as part of said biochemical test sequence comprises the step of rolling at least a portion of said absorbent material.

7. A method of sample processing as described in claim 6 wherein said step of rolling at least a portion of said absorbent material comprises the step of:
   a. rolling an unused portion of said absorbent material; and
   b. rolling a used portion of said absorbent material in coordination with said step of rolling an unused portion of said absorbent material.

8. A method of sample processing as described in claim 1 and further comprising the step of tensioning an unused portion of said absorbent material in an exposed position.

9. A method of sample processing as described in claim 1 and further comprising the step of encasing an absorbent material in a confinement enclosure.

10. A method of sample processing as described in claim 1 and further comprising automatically moving an absorbent material to a position in the vicinity of said sample holder.

11. A method of processing as described in claim 10 wherein said step of automatically moving an absorbent material to a position in the vicinity of said sample holder comprises the step of linearly moving an absorbent material to a position in the vicinity of said sample holder.

12. A method of processing as described in claim 11 and further comprising establishing said absorbent material in a median angular orientation relative to said sample.

13. A method of processing as described in claim 11 wherein said step of automatically moving an absorbent material to a position in the vicinity of said sample holder comprises the step of pressing said absorbent material past a point of initial contact.

14. A method of processing as described in claim 1 and further comprising the step of substantially eliminating a fluid environment from within the immediate vicinity of said sample.

15. A method of processing as described in claim 14 wherein said step of substantially eliminating a fluid environment from within the immediate vicinity of said sample comprises a step selected from the group consisting of:
   capillarly eliminating said fluid environment from within the immediate vicinity of said sample; and
   decreasing a restrictively confined fluidic environment in the vicinity of at least a portion of an exterior sample area.

16. A method of processing as described in claim 14 wherein said step of substantially eliminating said fluid environment from within the immediate vicinity of said sample comprises the step of decreasing a restrictively confined fluidic environment in the vicinity of at least a portion of an exterior sample area.

17. A method of processing as described in claim 1 and further comprising the steps of:
   a. transiently substantially eliminating said substance from said sample; and
   b. reapplying at least a portion of said transiently substantially eliminated substance to said sample.

18. A method as described in claim 17 wherein said step of transiently substantially eliminating said substance from said sample comprises the step of repeatedly transiently substantially eliminating said substance from said sample and wherein said step of reapplying at least a portion of said transiently substantially eliminated substance to said sample comprises the step of repeatedly reapplying at least a portion of said transiently substantially eliminated substance to said sample.

19. A method as described in claim 1 wherein the step of subjecting said sample to a substance comprises the steps of:
   subjecting said sample to a primary antibody substance;
   subjecting said sample to a secondary antibody substance; and
   subjecting said sample to a chromogen substance.

20. A method as described in claim 1 wherein the step of obtaining a sample comprises the step of obtaining a sample selected from a group consisting of:
   obtaining a biologic sample,
   obtaining a cellular sample, and
   obtaining a tissue sample.

21. A method as described in claim 1 wherein the step of obtaining a sample comprises a step of obtaining a thin biologic sample; and wherein the step of obtaining a thin biologic sample comprises a step of obtaining a biopsy sample.

22. A method as described in claim 1 and further comprising the step of establishing said sample on a surface of said sample holder.

23. A method as described in claim 22 wherein said step of establishing said sample on a surface of said sample holder comprise the step of establishing said sample on a substantially planar surface of said sample holder.

24. A method as described in claim 23 wherein said step of establishing said sample on a substantially planar surface of said sample holder comprises a step selected from a group consisting of:
   establishing said sample on a microscopic slide; and
   establishing said sample between at least two opposing microscopic slides.

25. A method as described in claim 24 wherein said step of establishing said sample on a microscopic slide comprises the step of establishing said sample between at least two opposing microscopic slides.

26. A method as described in claim 1 and further comprising a step selected from a group consisting of:
- configuring said process to be conducted in an automated fashion in an operating room time constraint environment,
- configuring said process to be conducted in an automated fashion in a point of care time constraint environment, and
- configuring said process to be conducted in an automated fashion in an surgery time constraint environment.

27. A method as described in claim 1 wherein said step of obtaining a sample comprises the step of obtaining a biopsy sample.

28. A method as described in claim 1 wherein said step of obtaining a sample comprises a step selected from a group consisting of:
- obtaining a carcinoma related sample,
- obtaining a melanoma related sample,
- obtaining a lymphoma related sample,
- obtaining a margin testing related sample,
- obtaining an epithelial cell sample,
- obtaining a lymph node sample,
- obtaining an undifferentiated tumor cell sample,
- obtaining a pediatric cell sample,
- obtaining a mohs mapping cell sample,
- obtaining an h.pylori cell sample,
- obtaining a chorionic villi tissue cell sample,
- obtaining a neonatal herpes cell sample,
- obtaining a proteomics sample,
- a step of providing a detection indication of the presence of a lymph node indicative substance within said sample,
- a step of providing a detection indication of the presence of a transplant procedure indicative substance within said sample,
- a step of providing a detection indication of the presence of a tumor differentiation indicative substance within said sample,
- a step of providing a detection indication of the presence of a pediatric pathology indicative substance within said sample,
- a step of providing a detection indication of the presence of a pediatric non-pathology indicative substance within said sample,
- a step of providing a detection indication of the presence of a mohs mapping indicative substance within said sample,
- a step of providing a detection indication of the presence of a margin indicative substance within said sample,
- a step of providing a detection indication of the presence of a h.pylori diagnosis indicative substance within said sample,
- a step of providing a detection indication of the presence of a therapeutic marker indicative substance within said sample,
- a step of providing a detection indication of the presence of a chorionic villi tissue indicative substance within said sample, and
- a step of providing a detection indication of the presence of a neonatal herpes indicative substance within said sample.

29. A method as described in claim 1 and further comprising the step of coordinating an absorbent material parameter to an anticipated adjacent multiple sample saturation level.

30. A method as described in claim 1 and further comprising the steps of:
- advancing said absorbent material in multiple sample appropriate increments; and
- tracking said multiple sample appropriate increments.

31. A method as described in claim 30 further comprising a step of tracking said multiple sample appropriate increments.

32. A method as described in claim 1 wherein said step of obtaining a sample comprises a step selected from a group consisting of:
- obtaining an epithelial cell sample,
- obtaining a lymph node sample,
- obtaining an undifferentiated tumor cell sample,
- obtaining a pediatric cell sample,
- obtaining a mohs mapping cell sample,
- obtaining an h.pylori cell sample,
- obtaining a chorionic villi tissue cell sample,
- obtaining a neonatal herpes cell sample, and
- obtaining a proteomics sample.

33. A method as described in claim 1 said step of obtaining a sample comprises a step selected from a group consisting of:
- a step of providing a detection indication of the presence of a lymph node indicative substance within said sample,
- a step of providing a detection indication of the presence of a transplant procedure indicative substance within said sample,
- a step of providing a detection indication of the presence of a tumor differentiation indicative substance within said sample,
- a step of providing a detection indication of the presence of a pediatric pathology indicative substance within said sample,
- a step of providing a detection indication of the presence of a pediatric non-pathology indicative substance within said sample,
- a step of providing a detection indication of the presence of a mohs mapping indicative substance within said sample,
- a step of providing a detection indication of the presence of a margin indicative substance within said sample,
- a step of providing a detection indication of the presence of a h.pylori diagnosis indicative substance within said sample,
- a step of providing a detection indication of the presence of a therapeutic marker indicative substance within said sample,
- a step of providing a detection indication of the presence of a chorionic villi tissue indicative substance within said sample, and
- a step of providing a detection indication of the presence of a neonatal herpes indicative substance within said sample.

34. A biochemical sample processor comprising:
a. a sample holder;
b. at least one substance source configured to permit the placement of a substance in the vicinity of a sample restrained by said sample holder;
c. at least some absorbent material;
d. an automatically sequenced biochemical test processor configured to automatically achieve a biochemical test sequence;
e. an absorbent material sequence element responsive to said automatically sequenced biochemical test processor, and to which said at least some absorbent material is responsive; and f. a substance withdrawal element configured to withdraw said substance upon completion of at least a portion of a process and that is responsive to said automatically sequenced biochemical test processor; wherein said substance withdrawal element is configured to extend to said substance in said vicinity of said sample restrained by said sample holder and retract from said substance in said vicinity of said sample restrained by said sample holder.

35. A biochemical sample processor as described in claim 34 wherein said absorbent material comprises a capillary action substance withdrawal element.

36. A biochemical sample processor as described in claim 35 wherein said capillary action substance withdrawal element comprises a wicking element.

37. A biochemical sample processor as described in claim 36 wherein said automatically sequenced biochemical test processor comprises a processor selected from a group consisting of:
- an immunohistochemical processor,
- an immunocytochemical processor,
- an in situ hybridization processor,
- a fluorescent in situ hybridization processor,
- a chromosomal identification processor,
- a staining processor,
- an antigen retrieval processor,
- a cytochemical processor,
- a histochemical processor,
- a molecular chemical processor,
- an epitope retrieval processor, and
- a pretreatment processor.

38. A biochemical sample processor as described in claim 34 wherein said absorbent material sequence element comprises a rotation element.

39. A biochemical sample processor as described in claim 38 wherein said absorbent material sequence element comprises an absorbent material roller system.

40. A biochemical sample processor as described in claim 39 wherein said absorbent material roller system comprises:
a. an unused portion roller; and
b. a used portion roller coordinated with said unused portion roller.

41. A biochemical sample processor as described in claim 34 and further comprising a confinement enclosure configured to substantially encase said absorbent material.

42. A biochemical sample processor as described in claim 34 and further comprising an absorbent material movement element responsive to said automatically sequenced biochemical test processor, and to which said at least some absorbent material is movably responsive.

43. A biochemical sample processor as described in claim 42 wherein said an absorbent material movement element comprises a linear absorbent material movement element.

44. A biochemical sample processor as described in claim 43 and further comprising a median angular orientation element which orients said absorbent material.

45. A biochemical sample processor as described in claim 43 wherein said linear absorbent material movement element comprises an absorbent material substance pressure element.

46. A biochemical sample processor as described in claim 34 wherein said absorbent material has a major axis, wherein said sample holder comprises a linearly arranged plural sample holder, and further comprising a parallel major axis orientation element that aligns said major axis parallel to said linearly arranged plural sample holder.

47. A biochemical sample processor as described in claim 34 wherein said absorbent material has an exposed area that is coordinated as appropriate for an anticipated amount of substance to be withdrawn.

48. A biochemical sample processor as described in claim 34 and further comprising a substance transient elimination element configured to substantially eliminate said substance from within an immediate vicinity of said sample.

49. A biochemical sample processor as described in claim 48 wherein said substance transient elimination element comprises a capillary action substance elimination element.

50. A biochemical sample processor as described in claim 48 wherein said capillary action substance elimination element comprises a decreasing restrictive fluidic confinement element.

51. A sample processor as described in claim 34 and further comprising:
a. a substance transient elimination element configured to substantially eliminate said substance from within the immediate vicinity of said sample; and
b. a substance reapplication element that acts upon at least a portion of said transiently eliminated substance.

52. A biochemical sample processor as described in claim 51 wherein said substance transient elimination element comprises a repetitious action substance transient elimination element, and wherein said substance reapplication element comprises a repetitious action substance reapplication element.

53. A sample processor as described in claim 34 wherein said sample holder comprises multiple sample holders and further comprising a substantially coincident sample treatment element to which said multiple sample holders are responsive.

54. A biochemical sample processor as described in claim 34 wherein said substance source comprises:
a. a primary antibody substance source,
b. a secondary antibody substance source, and
c. a chromogen substance source.

55. A biochemical sample processor as described in claim 34 wherein said automatically sequenced biochemical test processor is selected from a group consisting of:
- a sample processor configured to process a biologic sample,
- a sample processor configured to process a cellular sample, and
- a sample processor configured to process a tissue sample.

56. A biochemical sample processor as described in claim 34 wherein said sample holder comprises a thin biologic sample holder.

57. A biochemical sample processor as described in claim 34 wherein said thin biologic sample holder comprises a biopsy sample holder.

58. A biochemical sample processor as described in claim 34 wherein said sample holder comprises a surface.

59. A biochemical sample processor as described in claim 58 wherein said surface a substantially planar surface.

60. A biochemical sample processor as described in claim 34 wherein said sample holder comprises a microscopic slide.

61. A biochemical sample processor as described in claim 60 wherein said sample holder comprises at least two opposing microscopic slides.

62. A biochemical sample processor as described in claim 34 wherein said automatically sequenced biochemical test processor is selected from a group consisting of:
a sample processor configured to accomplish a process to be conducted in an automated fashion in an operating room time constraint environment, a sample processor configured to accomplish a process to be conducted in an automated fashion in a point of care time constraint environment, and a sample processor configured to accomplish a process to be conducted in an automated fashion in an surgery time constraint environment.

63. A biochemical sample processor as described in claim 34 wherein said sample holder comprises a biopsy sample holder and wherein said automatically sequenced biochemical test processor is configured to process a biopsy sample.

64. A biochemical sample processor as described in claim 34 wherein said sample holder comprises a biopsy sample holder and wherein said automatically sequenced biochemical test processor is configured to process a sample selected from a group consisting of:
 a carcinoma related sample,
 a melanoma related sample,
 a lymphoma related sample, and
 a margin testing related sample.

65. A biochemical sample processor as described in claim 34 wherein said automatically sequenced biochemical test processor is configured to process a sample selected from a group consisting of:
 an epithelial cell sample,
 a lymph node sample,
  an undifferentiated tumor cell sample,
  a pediatric cell sample,
 a mohs mapping cell sample,
 an h.pylori cell sample,
 a chorionic villi tissue cell sample,
 a neonatal herpes cell sample, and
 a proteomics sample.

66. A biochemical sample processor as described in claim 34 wherein said automatically sequenced biochemical test processor is configured to process a sample selected from a group consisting of:
 a transplant procedure indicative substance,
 a tumor differentiation indicative substance,
 a pediatric pathology indicative substance,
 a pediatric non-pathology indicative substance,
 a pathology indicative substance,
 a non-pathology indicative substance,
 a margin indicative substance, and
 a therapeutic marker indicative substance.

67. A biochemical sample processor as described in claim 34 wherein said absorbent material has a multiple sample saturation coordinated parameter.

68. A biochemical sample processor as described in claim 34 further comprising an absorbent material multiple sample appropriate incremental advance element.

69. A biochemical sample processor as described in claim 68 further comprising a multiple sample appropriate increment tracker element.

* * * * *